United States Patent [19]

Saino et al.

[11] Patent Number: 5,591,633
[45] Date of Patent: Jan. 7, 1997

[54] NUCLEIC ACIDS ENCODING HUMAN PLACENTAL COAGULATION INHIBITOR (PCI)

[75] Inventors: Yushi Saino, Tokyo; Akio Iwasaki, Kawasaki; Makoto Suda, Tsukuba, all of Japan

[73] Assignee: Kowa Co., Ltd., Nagoya, Japan

[21] Appl. No.: 125,746

[22] Filed: Sep. 24, 1993

Related U.S. Application Data

[62] Division of Ser. No. 807,623, Dec. 13, 1991, abandoned, which is a continuation of Ser. No. 156,822, Feb. 17, 1988, abandoned.

[30] Foreign Application Priority Data

Feb. 20, 1987 [JP] Japan .................................. 62-037227
Jul. 23, 1987 [JP] Japan .................................. 62-184428

[51] Int. Cl.⁶ ............................. C12N 15/12; C12N 1/11; C12N 5/10
[52] U.S. Cl. .................................... 435/252.3; 435/320.1; 435/172.3; 435/240.1; 536/23.5
[58] Field of Search ...................... 536/23.5; 435/320.1, 435/69.1, 252.3, 240.1

[56] References Cited

U.S. PATENT DOCUMENTS 4,937,324  6/1990  Fujikawa et al. ........................ 530/397

OTHER PUBLICATIONS

Maniatis et al. 1982. *Molecular Cloning*, Cold Spring Harbor Lab. Press, NY. pp. 403–433.
Suggs et al. 1981. PNAS USA 78: 6613–7.

*Primary Examiner*—John Ulm
*Assistant Examiner*—Elizabeth C. Kemmerer
*Attorney, Agent, or Firm*—Oblon, Spivak, McClelland, Maier & Neustadt, P.C.

[57] ABSTRACT

A polypeptide having a specific amino acid sequence is described. Also described are a novel DNA coding the polypeptide, a recombinant plasmid containing the DNA, a transformant containing the recombinant plasmid, an anticoagulant containing the polypeptide as an effective ingredient, and a process for the production of the polypeptide.

6 Claims, 6 Drawing Sheets

```
-135  GGATCCTTCAGGTCTGCATCTCGGGTGCCCCGTGCGCCCGGCTCTC

-80  CGCCGGCTCTCCCGGGGTTCGGGGCACTTGGGTCCCACAGTCTGGTCCTGCTTCACCTTCCCTGACCTGAGTAGTCGCC

1  ATG GCA CAG GTT CTC AGA GGC ACT GTG ACT GAC TTC CCT GGA TTT GAT GAG CGG GCT GAT
      MET Ala Gln Val Leu Arg Gly Thr Val Thr Asp Phe Pro Gly Phe Asp Glu Arg Ala Asp
      NcoI

61  GCA GAA ACT CTT CGG AAG GCT ATG AAA GGC TTG GGC ACA GAT GAG GAG AGC ATC CTG ACT
      Ala Glu Thr Leu Arg Lys Ala Met Lys Gly Leu Gly Thr Asp Glu Glu Ser Ile Leu Thr

121  CTG TTG ACA TCC CGA AGT AAT GCT CAG CGC CAG GAA ATC TCT GCA GCT TTT AAG ACT CTG
      Leu Leu Thr Ser Arg Ser Asn Ala Gln Arg Gln Glu Ile Ser Ala Ala Phe Lys Thr Leu
                                                              PstI

181  TTT GGC AGG GAT CTT CTG GAT GAC CTG AAA TCA GAA CTA ACT GGA AAA TTT GAA AAA TTA
      Phe Gly Arg Asp Leu Leu Asp Asp Leu Lys Ser Glu Leu Thr Gly Lys Phe Glu Lys Leu

241  ATT GTG GCT CTG ATG AAA CCC TCT CGG CTT TAT GAT GCT TAT GAA CTG AAA CAT GCC TTG
      Ile Val Ala Leu Met Lys Pro Ser Arg Leu Tyr Asp Ala Tyr Glu Leu Lys His Ala Leu

301  AAG GGA GCT GGA ACA AAT GAA AAA GTA CTG ACA GAA ATT ATT GCT TCA AGG ACA CCT GAA
      Lys Gly Ala Gly Thr Asn Glu Lys Val Leu Thr Glu Ile Ile Ala Ser Arg Thr Pro Glu

361  GAA CTG AGA GCC ATC AAA CAA GTT TAT GAA GAA GAA TAT GGC TCA AGC CTG GAA GAT GAC
      Glu Leu Arg Ala Ile Lys Gln Val Tyr Glu Glu Glu Tyr Gly Ser Ser Leu Glu Asp Asp
```

*FIG. 2a*

```
421  GTG GTG GGG GAC ACT TCA GGG TAC TAC CAG CGG ATG TTG GTG GTT CTC CTT CAG GCT AAC
     Val Val Gly Asp Thr Ser Gly Tyr Tyr Gln Arg Met Leu Val Val Leu Leu Gln Ala Asn

481  AGA GAC CCT GAT GCT GGA ATT GAT GAA GCT CAA GTT GAA CAA GAT GCT CAG GCT TTA TTT
     Arg Asp Pro Asp Ala Gly Ile Asp Glu Ala Gln Val Glu Gln Asp Ala Gln Ala Leu Phe

541  CAG GCT GGA GAA CTT AAA TGG GGG ACA GAT GAA GAA AAG TTT ATC ACC ATC TTT GGA ACA
     Gln Ala Gly Glu Leu Lys Trp Gly Thr Asp Glu Glu Lys Phe Ile Thr Ile Phe Gly Thr

601  CGA AGT GTG TCT CAT TTG AGA AAG GTG TTT GAC AAG TAC ATG ACT ATA TCA GGA TTT CAA
     Arg Ser Val Ser His Leu Arg Lys Val Phe Asp Lys Tyr Met Thr Ile Ser Gly Phe Gln

661  ATT GAG GAA ACC ATT GAC CGC ATT CGA GAG ACT TCT GGC AAT TTA GAG CAA CTA CTC CTT GCT GTT
     Ile Glu Glu Thr Ile Asp Arg Ile Arg Glu Thr Ser Gly Asn Leu Glu Gln Leu Leu Leu Ala Val

721  GTG AAA TCT ATT CGA AGT ATA CCT GCA GAG ACC CTC TAT TAT GCT ATG AAG
     Val Lys Ser Ile Arg Ser Ile Pro Ala Glu Thr Leu Tyr Tyr Ala Met Lys

781  GGA GCT GGG ACA GAT GAT CAT GAT ACC CTC ATC AGA GTC ATG GTT TCC AGG AGT GAG ATT GAT
     Gly Ala Gly Thr Asp Asp His Asp Thr Leu Ile Arg Val Met Val Ser Arg Ser Glu Ile Asp

841  CTG TTT AAC ATC AGG AAG GAG TTT AGG AAG AAT TTT GCC ACC TCT CTT TAT TCC ATG ATT
     Leu Phe Asn Ile Arg Lys Glu Phe Arg Lys Asn Phe Ala Thr Ser Leu Tyr Ser Met Ile

901  AAG GGA GAT ACA TCT GGG GAC TAT AAG AAA GCT CTT CTG CTC TGT GGA GAA GAT GAC
     Lys Gly Asp Thr Ser Gly Asp Tyr Lys Lys Ala Leu Leu Leu Cys Gly Glu Asp Asp
```

*FIG. 2b*

```
 961  TAACGTGTGTCACGGGGAAGAGCTCCCTGCTGTGTGCCTGCACCACCCCACTGCCTTCCTTCAGCACCTTTAGCTGCATTTG
                         SacI
      ***
1041  TATGCCAGTGCTTAACACATTGCCTTATTCATACTAGCATGCTCATGACCAACACATACACGTCATAGAGAAGAAAATAGTG
                                             SphI
1121  GTGCTTCTTTCTGATCTCTTTGACTGCTGTAGTACTAAAGTGTACTTAATGTTACTAAGTTAATGC
1201  CTGGCCATTTTCCATTTATATATATTTTTAAGAGGCTAGAGTGCTTTAGCCTTTTTTAAAAACTCCATTATATTACA
1281  TTTGTAACCATGATACTTTAATCAGAAGCTTAGCCTTGAAATTGTGAACTCTTGGAAATGTTATTAGTGAAGTTCGCAAC
                                    HindIII
1361  TAAACTAAACCTGTAAAATTATGATGATTGTATTCAAAAGATTAATGAAAAATAAACATTTCTGTCCCCCTG(poly A)
```

FIG. 2c

NUCLEIC ACIDS ENCODING HUMAN PLACENTAL COAGULATION INHIBITOR (PCI)

This is a division of application Ser. No. 07/807,623, filed on Dec. 13, 1991 now abandoned, which is a continuation of application Ser. No. 07/156,822, filed on Feb. 17, 1988, now abandoned.

BACKGROUND OF THE INVENTION

1) Field of the Invention

This invention relates to a polypeptide having anticoagulant activities like a placental coagulation inhibitor (hereinafter called "PCI") available from human tissues led by the human placenta, a novel DNA coding the polypeptide, a recombinant plasmid containing the DNA, a transformant containing the recombinant plasmid, an anticoagulant containing the polypeptide as an effective ingredient and a process for the production of the polypeptide.

2) Description of the Prior Art

Heparin, heparin cofactor-II, antithrombin-III, $\alpha_2$-macroglobulin, $\alpha_1$-trypsin inhibitor, $C_1$-esterase inhibitor, protein C and the like have conventionally been known as anticoagulants. It is however only heparin that has found practical utility. Heparin however has a side effect of inducing bleeding tendency. Extremely stringent limitations are therefore imposed on its manner of administration and its dosage. Heparin has hence been not satisfactory as an anticoagulant from the standpoint of safety.

Under the aforementioned circumstances, the present applicant has already succeeded in separating and purifying PCI from the human placenta, on which an application has been filed (Japanese Patent Application No. 217512/1985).

PCI is a substance which has the following properties and is useful as a medicine.

(1) Molecular weight (SDS-polyacrylamide gel electrophoresis, reduced state): 34,000±2,000.

(2) Isoelectric point (isoelectric column electrophoresis using an ampholyte): 4.7±0.1.

(3) Stability:
 (a) Inactivated by a heat treatment at 50° C. for 30 minutes.
 (b) Stable in a pH range of 4–10.
 (c) Stable in plasma at 37° C. for 30 minutes.

(4) Effects:
 (a) Capable of prolonging the recalcification time.
 (b) Capable of prolonging the prothrombin time.
 (c) Capable of prolonging the activated partial thromboplastin time.

(5) Analysis of amino acids:
 The existence of aspartic acid, threonine, serine, glutamic acid, proline, glycine, alanine, ½ cystine, valine, methionine, isoleucine, leucine, tyrosine, phenylalanine, histidine, lysine and arginine is recognized by the analysis of amino acids.

The present applicant has also prepared a monoclonal antibody specific to PCI and already filed an application for patent thereon (Japanese Patent Application No. 269588/1986). It is feasible to perform high-sensitivity assay, purification, etc. of the PCI by using this monoclonal antibody.

Several problems have however arisen because human tissues typified by human placentae are presently indispensable as a raw material for obtaining PCI. For example, there is a limitation imposed on the quantity of PCI available from a human tissue. Difficulties are always accompanied upon collection of human tissues as a raw material, whereby stable supply of the raw material is difficult. In addition, the potential danger of pathogenic viruses which may be contained in human tissues is not ignorable.

It has hence been desired to develop a method for supplying PCI at a lower price, in a larger volume, more stably and more safely or to develop a substance having effects similar to PCI.

SUMMARY OF THE INVENTION

The present inventors have proceeded with an extensive investigation with a view toward solving these problems. As a result, it has been found that a DNA fragment capable of coding the PCI peptide can be obtained from the human placental cDNA library by using the PCI-specific antibody as a probe and a PCI-like polypeptide can also be produced by transforming cells of a microorganism with a recombinant plasmid, in which the DNA fragment has been incorporated, and then allowing the resultant transformant to express the PCI gene, leading to completion of the present invention.

This invention therefore provides a polypeptide having the following amino acid sequence:(SEQ ID NO:2)

Ala—Gln—Val—Leu—Arg—Gly—Thr—Val—Thr—Asp—Phe—Pro
Gly—Phe—Asp—Glu—Arg—Ala—Asp—Ala—Glu—Thr—Leu—Arg
Lys—Ala—Met—Lys—Gly—Leu—Gly—Thr—Asp—Glu—Glu—Ser
Ile—Leu—Thr—Leu—Leu—Thr—Ser—Arg—Ser—Asn—Ala—Gln
Arg—Gln—Glu—Ile—Ser—Ala—Ala—Phe—Lys—Thr—Leu—Phe
Gly—Arg—Asp—Leu—Leu—Asp—Asp—Leu—Lys—Ser—Glu—Leu
Thr—Gly—Lys—Phe—Glu—Lys—Leu—Ile—Val—Ala—Leu—Met
Lys—Pro—Ser—Arg—Leu—Tyr—Asp—Ala—Tyr—Glu—Leu—Lys
His—Ala—Leu—Lys—Gly—Ala—Gly—Thr—Asn—Glu—Lys—Val
Leu—Thr—Glu—Ile—Ile—Ala—Ser—Arg—Thr—Pro—Glu—Glu
Leu—Arg—Ala—Ile—Lys—Gln—Val—Tyr—Glu—Glu—Glu—Tyr
Gly—Ser—Ser—Leu—Glu—Asp—Asp—Val—Val—Gly—Asp—Thr
Ser—Gly—Tyr—Tyr—Gln—Arg—Met—Leu—Val—Val—Leu—Leu
Gln—Ala—Asn—Arg—Asp—Pro—Asp—Ala—Gly—Ile—Asp—Glu
Ala—Gln—Val—Glu—Gln—Asp—Ala—Gln—Ala—Leu—Phe—Gln
Ala—Gly—Glu—Leu—Lys—Trp—Gly—Thr—Asp—Glu—Glu—Lys
Phe—Ile—Thr—Ile—Phe—Gly—Thr—Arg—Ser—Val—Ser—His
Leu—Arg—Lys—Val—Phe—Asp—Lys—Tyr—Met—Thr—Ile—Ser
Gly—Phe—Gln—Ile—Glu—Glu—Thr—Ile—Asp—Arg—Glu—Thr
Ser—Gly—Asn—Leu—Glu—Gln—Leu—Leu—Leu—Ala—Val—Val
Lys—Ser—Ile—Arg—Ser—Ile—Pro—Ala—Tyr—Leu—Ala—Glu
Thr—Leu—Tyr—Tyr—Ala—Met—Lys—Gly—Ala—Gly—Thr—Asp
Asp—His—Thr—Leu—Ile—Arg—Val—Met—Val—Ser—Arg—Ser
Glu—Ile—Asp—Leu—Phe—Asn—Ile—Arg—Lys—Glu—Phe—Arg
Lys—Asn—Phe—Ala—Thr—Ser—Leu—Tyr—Ser—Met—Ile—Lys
Gly—Asp—Thr—Ser—Gly—Asp—Tyr—Lys—Lys—Ala—Leu—Leu
Leu—Leu—Cys—Gly—Glu—Asp—Asp, a novel DNA coding the polypeptide, a recombinant plasmid containing the DNA, a transformant containing the recombinant plasmid, an anticoagulant containing the polypeptide as an effective ingredient, and a process for the production of the polypeptide.

Since the polypeptide of this invention exhibits strong anticoagulant activities, an anticoagulant containing it as an effective ingredient is useful for the prevention and treatment of various diseases caused by exasperation of coagulative activities, for example, thromboses, DIC (disseminated intravascular coagulation) and the like in the brain, heart and peripheral blood vessels, such as cerebral infarction and myocardial infarction.

In addition, the polypeptide of this invention has properties similar to those of the placental coagulation inhibitor (PCI) derived from the human placenta. It is hence a safe substance having no antigenecity against men. In spite of the fact that PCI is useful as an anticoagulant, it is accompanied by the drawback that it cannot be produced in any large volume due to difficulties in the availability of human placentae. In contrast, the polypeptide of this invention can be produced in a large volume and at a low price.

The above and other objects, features and advantages of the present invention will become apparent from the following description and the appended claims, taken in conjunction with the accompanying drawings.

BRIEF DESCRIPTION OF THE DRAWINGS

FIG. 2 is a schematic illustration of the nucleotide sequence (SEQ ID NO:2) of PCI cDNA according to this invention, in which the nucleotides are successively numbered labelling A of the translation starting codon ATG as No. 1.

DETAILED DESCRIPTION OF THE INVENTION

Figure 1:
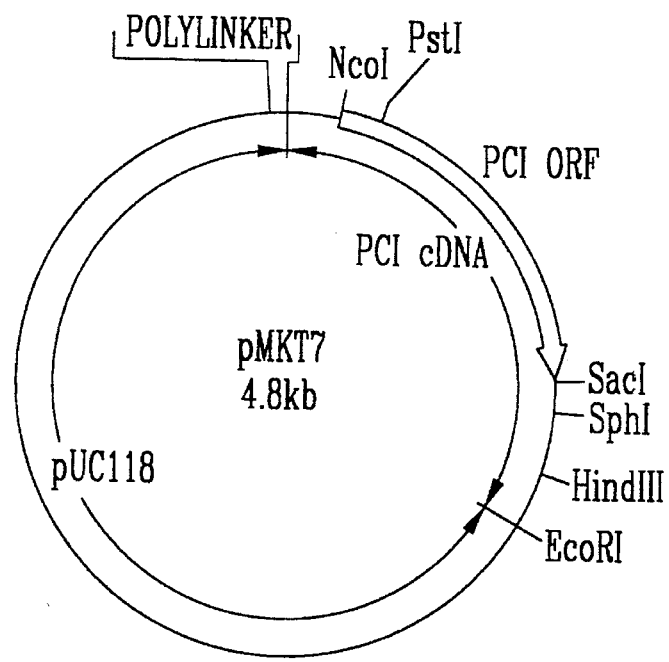
FIG. 1 is a sketch showing the restriction endonuclease map of the recombinant plasmid pMKT7 of this invention.

The DNA coding the polypeptide of this invention, the recombinant plasmid and the transformant may be produced, for example, in the following manner.

Namely, (1) an antibody-positive clone is screened out from the human placenta cDNA library by using the PCI-specific antibody. (2) The recombinant DNA is prepared from the antibody-positive clone thus isolated, and cDNA fragments are spliced from the recombinant phage DNA by treating the latter with a restriction endonuclease and are then incorporated in a plasmid vector. (3) Host cells are transformed with the resulting cDNA recombinant plasmid, thereby obtaining transformants of this invention. The thus-obtained transformants of this invention are cultured, whereby a recombinant plasmid of this invention which contains the DNA fragment of this invention is obtained from cells thus cultured. DNA fragments according to this invention may then be obtained by cleaving the thus-obtained recombinant plasmids with a suitable restriction endonuclease.

The above steps will next be described individually.
(1) Screening of the antibody-positive clone from the human placenta cDNA library:

The cDNA library may be prepared by preparing mRNA from a human placenta and then treating mRNA with a reverse transcriptase and a suitable vector DNA. Commercial cDNA library, for example, the human placental cDNA library (λgt11) produced by Clontech Laboratories, Inc. may also be used as an alternative.

The cDNA library prepared using λgt11as a vector may be subjected to screening by using a particular antibody as a probe in accordance with a method proposed by Young and Davis [Huynh, T. V., Young, R. A. and Davis, R. W. (1985) In: *DNA Cloning: A Practical Approach*, vol. 1, (D. M. Glover, ed.), pp 49–78, IRL Press, Oxford], so that a clone specific to the particular antibody may be isolated.

As primary antibodies useful as probes, may be mentioned PCI-specific antibodies, e.g., anti-PCI rabbit polyclonal antibody, anti-PCI mouse polyclonal antibody and anti-PCI monoclonal antibodies. Of these, anti-PCI monoclonal antibodies, especially, anti-PCI mouse monoclonal antibody is preferred. The antibody may be used in any one of serum, ascitic fluid, hybridoma culture fluid, purified immunoglobulin forms.

The detection of a primary antibody conjugated with an antigen may be performed by autoradiography, which makes use of protein A labelled with radioactive iodine ($^{125}$I) or an Anti-immunoglobulin antibody labelled with radioactive iodine (125I), or by enzyme immunoassay in which an anti-immunoglobulin antibody labelled with a peroxidase or an anti-immunoglobulin antibody labelled with an alkaline phosphatase.

Incidentally, the anti-PCI monoclonal antibody may be produced, for example, by the process described in Japanese Patent Application No. 269588/1986 referred to above. Namely, a mouse is immunized with PCI which has been purified subsequent to its extraction from human placentae. Spleen cells are collected from the mouse and are then caused to undergo cell fusion with mouse myeloma cells. The cells, which have been subjected to the cell fusion, are cultured using an HAT selective medium, whereby hybridomas are alone allowed to multiply. Using PCI as an antigen, the culture with the hybridomas thus multiplied is thereafter subjected to screening by enzyme immunoassay, thereby obtaining a hybridoma capable of producing a monoclonal antibody specific to PCI. The monoclonal antibody is obtained from a culture in which the hybridoma thus obtained has been cultured or from the ascitic fluid of a mouse which has been inoculated the hybridoma.
(2) Preparation of PCI cDNA recombinant plasmid:

Recombinant λgt11phage DNA is extracted in a purified form from the thus-isolated antibody-positive clone in accordance with the method proposed by Perbal [Bernard Perbal, PREPARATION OF λ PHAGE DNA in A PRACTICAL GUIDE TO MOLECULAR CLONING, pp 175–184, A Willey-Interscience Publication (1984), New York, U.S.A.]. cDNA can be separated from the vector DNA by digesting the thus-purified recombinant λgt11phage DNA with a restriction endonuclease EcoRI. The resultant cDNA is caused to rejoin with various cloning plasmid vectors which have been obtained by digesting with EcoRI, whereby recombinant plasmids are prepared. As usable plasmid vectors, pBR322, pBR325, pUC18, pUC118, pTZ18R and the like may be mentioned by way of example.
(3) Transformation of host cells with the PCI cDNA recombinant plasmid as well as preparation of recombinant plasmid of this invention and DNA of the present invention:

The resultant PCI cDNA recombinant plasmid is introduced into various host cells capable of using to the maximum extent the gene marker which the recombinant plasmid has, whereby the host cells are transformed. As host cells, *E. coli* is preferred. Various variants of *E. coli* K12 strain, for example, HB101, C600K, JM101, JM105, X1776, MV1304 and the like may be used. The competent cell method relying upon a calcium treatment or a like method may be used for the introduction of the recombinant plasmid.

The transformant is then cultured in a selective medium suitable for the gene marker of the vector plasmid and the recombinant plasmid of this invention is harvested from the cells.

Where pUC118 or pTZ18R is used as a vector, a single-stranded DNA can be prepared by infecting with a helper phage M13K07 the resultant transformant of *E. coli*, which contains the recombinant vector. The DNA base sequence of the resultant single-stranded DNA can be determined by the dideoxynucleotide chain termination method [Sanger, F., Nicklen, S. and Coulson, A.R.: DNA Sequencing with Chain Terminating Inhibitors, Proc. Natl. Aca. Sci. USA, 74, 5463–5467 (1977)].

In the above nucleotide sequence, the nucleotide sequence of the part coding the polypeptide, one of intended substances in the present invention, may be represented by way of example as follows:(SEQ ID NO:4)

```
GCACAGGTTC TCAGAGGCAC TGTGACTGAC TTCCCTGGAT
TTGATGAGCG GGCTGATGCA GAAACTCTTC GGAAGGCTAT
GAAAGGCTTG GGCACAGATG AGGAGAGCAT CCTGACTCTG
TTGACATCCC GAAGTAATGC TCAGCGCCAG GAAATCTCTG
CAGCTTTTAA GACTCTGTTT GGCAGGGATC TTCTGGATGA
CCTGAAATCA GAACTAACTG GAAAATTTGA AAAATTAATT
GTGGCTCTGA TGAAACCCTC TCGGCTTTAT GATGCTTATG
AACTGAAACA TGCCTTGAAG GGAGCTGGAA CAAATGAAAA
AGTACTGACA GAAATTATTG CTTCAAGGAC ACCTGAAGAA
CTGAGAGCCA TCAAACAAGT TTATGAAGAA GAATATGGCT
CAAGCCTGGA AGATGACGTG GTGGGGGACA CTTCAGGGTA
CTACCAGCGG ATGTTGGTGG TTCTCCTTCA GGCTAACAGA
GACCCTGATG CTGGAATTGA TGAAGCTCAA GTTGAACAAG
ATGCTCAGGC TTTATTTCAG GCTGGAGAAC TTAAATGGGG
GACAGATGAA GAAAAGTTTA TCACCATCTT TGGAACACGA
AGTGTGTCTC ATTTGAGAAA GGTGTTTGAC AAGTACATGA
CTATATCAGG ATTTCAAATT GAGGAAACCA TTGACCGCGA
GACTTCTGGC AATTTAGAGC AACTACTCCT TGCTGTTGTG
AAATCTATTC GAAGTATACC TGCCTACCTT GCAGAGACCC
TCTATTATGC TATGAAGGGA GCTGGGACAG ATGATCATAC
CCTCATCAGA GTCATGGTTT CCAGGAGTGA GATTGATCTG
TTTAACATCA GGAAGGAGTT TAGGAAGAAT TTTGCCACCT
CTCTTTATTC CATGATTAAG GGAGATACAT CTGGGGACTA
TAAGAAAGCT CTTCTGCTGC TCTGTGGAGA AGATGAC.
```

The DNA fragment of this invention is not necessarily limited to the above nucleotide sequence so long as it has ability to code the amino acid sequence described above. The recombinant plasmid of this invention may result from ligation with any vector DNA derived from *E. coli*, *B. subtilis*, yeast or the like, provided that the recombinant plasmid of this invention has a nucleotide sequence capable of coding the above-described amino acid sequence and is replicative.

The polypeptide according to this invention can be produced by culturing a transformant containing the recombinant plasmid of this invention and harvesting the polypeptide from the resultant culture. For the efficient production of polypeptide of this invention, it is however necessary to construct a plasmid for expression of PCI cDNA, which contains the following regions (1)–(6) in order in the downstream direction of transcription:

(1) a promoter, (2) a ribosome-binding site, (3) an initiation codon, (4) a DNA having a nucleotide sequence capable of coding the amino acid sequence of the polypeptide of this invention, (5) a termination codon, and (6) a transcription terminator, and then to transform host cells with the plasmid cloning vector.

As a vector host for obtaining such a plasmid for expression of PCI cDNA, a unicellular microorganism such as bacteria, notably, *E. coli*, *B. subtilis* or Streptomyces is preferred. When *E. coli* is chosen as a host, various variants of the K12 strain of *E. coli*, for example, HB101, C600K, JM101, JM105, JM109, X1776, MV1304 and the like may be used.

DNA used as a vector may preferably be plasmid. Where *E. coli* is used as a host by way of example, plasmid DNA has a DNA sequence required for the multiplication of the plasmid in cells of *E. coli*, for example, the DNA sequence of the starting region of replication of ColE1 plasmid and also has another DNA sequence capable of serving as a promoter and transcription terminator. It is more preferable that the plasmid DNA contains a gene capable of acting as a selective marker in a transformant of *E. coli*. Illustrative examples of the promoter may include promotors such as λPL, lac, trp, tac, trc and lpp. As an exemplary transcription terminator, may be mentioned rrnB ribosomal RNA transcription terminator or the like. As selective marker genes, may be mentioned ampicillin-resistant genes, kanamycin-resistant genes, tetracycline-resistant genes, chloramphenicol-resistant genes and so on. These genes may be used either singly or in combination.

The incorporation of a DNA having a nucleotide sequence capable of coding the amino acid sequence of the polypeptide of this invention, namely, the DNA fragment of this invention, into the above-described vector DNA may be effected by cleaving the DNA with a suitable restriction endonuclease and after adding a suitable linker if needed, joining the resultant DNA fragment with a vector DNA which has been cleaved with a suitable restriction endonuclease. In the case of a DNA having the base sequence of FIG. 2 (SEQ ID NO:2) for example, Nco I and Sac I, Nco I and Sph I, Nco I and Hind III, or the like may be mentioned as restriction endonucleases.

Introduction of the resultant plasmid for expression of PCI cDNA into host cells by the competent cell method, protoplasts method, calcium coprecipitation method, electric pulse method or the like permits production of a transformant which has ability to produce the polypeptide of this invention efficiently.

The polypeptide of this invention can be produced by culturing the resultant transformant and then extracting and isolating the polypeptide from the thus-cultured cells and/or the resulting culture.

Upon culture of the transformant, various natural and synthetic culture media may be employed. The medium may desirably contain carbon sources such as sugar, alcohol or organic acid salt; nitrogen sources such as protein mixture, amino acids or ammonium salt, and inorganic salts. It is also desired to add vitamins and an antibiotic corresponding to the associated selective marker gene. If the plasmid allows to control the expression, it is necessary to perform a procedure in the course of culturing so as to induce the expression. After the culture, centrifugation is conducted to separate the resultant culture broth into culture and cultured cells. Where the polypeptide of this invention accumulates in the cells cultured, it is necessary to disrupt or fracture the cells by freeze thawing, ultrasonic processing, French press, enzyme treatment, homogenizer or the like and then to solubilize the polypeptide of this invention, for example, with EDTA, surfactant, urea, guanidine hydrochloride or the like.

The resultant culture or cultured cell extract, which contains the polypeptide of this invention, is subjected to chromatography on one of various columns, so that the polypeptide of this invention can be obtained in a purified form. As column chromatography, ion-exchange chromatography, affinity chromatography and gel chromatography may be applied either singly or in combination.

The thus-obtained polypeptide of this invention has the following properties.

(1) Amino acid sequence:

Using a "JEOL JAS-570K Sequence Analyzer" (trade name; manufactured by JEOL Ltd.), the amino acid sequence of an N-terminal region was analyzed by converting the N-terminal region into PTH amino acid. As a result, the sequence of ten amino acids from the N-terminal of the polypeptide of this invention was determined as follows:(SEQ ID NO:5)

Ala-Gln-Val-Leu-Arg-Gly-Thr-Val-Thr-AsP

As a result, the amino acid sequence of the polypeptide of this invention can be estimated as follows (SEQ ID NO:1) from the base sequence of the DNA fragment of this invention:

Ala—Gln—Val—Leu—Arg—Gly—Thr—Val—Thr—Asp—Phe—Pro
Gly—Phe—Asp—Glu—Arg—Ala—Asp—Ala—Glu—Thr—Leu—Arg
Lys—Ala—Met—Lys—Gly—Leu—Gly—Thr—Asp—Glu—Glu—Ser
Ile—Leu—Thr—Leu—Leu—Thr—Ser—Arg—Ser—Asn—Ala—Gln
Arg—Gln—Glu—Ile—Ser—Ala—Ala—Phe—Lys—Thr—Leu—Phe
Gly—Arg—Asp—Leu—Leu—Asp—Asp—Leu—Lys—Ser—Glu—Leu
Thr—Gly—Lys—Phe—Glu—Lys—Leu—Ile—Val—Ala—Leu—Met
Lys—Pro—Ser—Arg—Leu—Tyr—Asp—Ala—Tyr—Glu—Leu—Lys
His—Ala—Leu—Lys—Gly—Ala—Gly—Thr—Asn—Glu—Lys—Val
Leu—Thr—Glu—Ile—Ile—Ala—Ser—Arg—Thr—Pro—Glu—Glu
Leu—Arg—Ala—Ile—Lys—Gln—Val—Tyr—Glu—Glu—Glu—Tyr
Gly—Ser—Ser—Leu—Glu—Asp—Asp—Val—Val—Gly—Asp—Thr
Ser—Gly—Tyr—Tyr—Gln—Arg—Met—Leu—Val—Val—Leu—Leu
Gln—Ala—Asn—Arg—Asp—Pro—Asp—Ala—Gly—Ile—Asp—Glu
Ala—Gln—Val—Glu—Gln—Asp—Ala—Gln—Ala—Leu—Phe—Gln
Ala—Gly—Glu—Leu—Lys—Trp—Gly—Thr—Asp—Glu—Glu—Lys
Phe—Ile—Thr—Ile—Phe—Gly—Thr—Arg—Ser—Val—Ser—His
Leu—Arg—Lys—Val—Phe—Asp—Lys—Tyr—Met—Thr—Ile—Ser
Gly—Phe—Gln—Ile—Glu—Glu—Thr—Ile—Asp—Arg—Glu—Thr
Ser—Gly—Asn—Leu—Glu—Gln—Leu—Leu—Leu—Ala—Val—Val
Lys—Ser—Ile—Arg—Ser—Ile—Pro—Ala—Tyr—Leu—Ala—Glu
Thr—Leu—Tyr—Tyr—Ala—Met—Lys—Gly—Ala—Gly—Thr—Asp
Asp—His—Thr—Leu—Ile—Arg—Val—Met—Val—Ser—Arg—Ser
Glu—Ile—Asp—Leu—Phe—Asn—Ile—Arg—Lys—Glu—Phe—Arg
Lys—Asn—Phe—Ala—Thr—Ser—Leu—Tyr—Ser—Met—Ile—Lys
Gly—Asp—Thr—Ser—Gly—Asp—Tyr—Lys—Lys—Ala—Leu—Leu
Leu—Leu—Cys—Gly—Glu—Asp—Asp.

(2) Molecular weight:

35,805 (calculated from the amino acid sequence).

34,000±1,000 (SDS-polyacrylamide gel electrophoresis, reduced state)

(3) Isoelectric point (isoelectric electrophoresis using an ampholyte):

5.0±0.1.

(4) Stability:

Stable in plasma at 37° C. for 30 minutes.

(5) Effects:

(a) Capable of prolonging the recalcification time.

(b) Capable of prolonging the prothrombin time.

(c) Capable of prolonging the activated partial thromboplastin time.

As has been described above, the polypeptide of this invention has excellent anticoagulant activities and is hence useful as an anticoagulant.

As a dosage form upon using the polypeptide of this invention as an effective ingredient for an anticoagulant, an injection may be mentioned. As the injection, it is preferable to form the polypeptide into lyophilized powder so that whenever needed, the polypeptide may be dissolved in distilled water for injection, physiological saline or the like for administration. The suitable route of its administration is intravenous.

Although the dose of the polypeptide varies depending on the severity of disease, the body weight of each patient, etc., it is generally preferable to administer it at 10 μg–10 mg/kg·day. The polypeptide of this invention does not develop any appreciable abnormality and is safe so long as it is administered within the above dose range.

Having generally described the invention, a more complete understanding can be obtained by reference to certain specific examples, which are provided herein for purposes of illustration only and are not intended to be limiting unless otherwise specified.

EXAMPLES

The present invention will hereinafter be described with reference to the following Referential Example and Examples.

Referential Example: Preparation of Anti-PCI Monoclonal Antibody (1) Purification of antigen (PCI):

(a) Five human placentae (about 2,500 g) were minced subsequent to removal of membranes and the like and thorough washing with a physiological saline. The thus-minced placentae were ground in a Waring blender and then added with 2 l of a 50 mM tris-hydrochloric acid buffer (pH 7.4), followed by further comminution in "Polytron". The resulting homogenate was subjected to centrifugal separation at 7,000 r.p.m. for 15 minutes to collect a sediment. Two liters of the 50 mM tris-hydrochloric acid buffer (pH 7.4) were added again to the thus-collected sediment, and the resulting mixture was homogenized in "Polytron" and then subjected to centrifugal separation at 7,000 r.p.m. for 15 minutes to obtain a washed sediment. The above procedure was repeated several times until blood components were removed to obtain about 930 g of a washed sediment finally.

(b) About 2 liters of a 50 mM tris-hydrochloric acid buffer (pH 7.4) containing 50 mM of EDTA were added to 900 g of the sediment obtained in the above procedure (a), followed by homogenization in the Waring blender. The resulting homogenate was agitated over-night at 4° C., followed by centrifugal separation at 7,000 r.p.m. for 15 minutes to obtain 2 liters of an extract.

(c) Solid ammonium sulfate was added to the extract obtained in the above procedure (b) to 35% of its saturated concentration. After allowing the resultant mixture to stand at 4° C. for 30 minutes to several hours, it was centrifuged at 7,000 r.p.m. for 15 minutes to collect a supernatant. Ammonium sulfate was added further to the supernatant to 85% of its saturated concentration. The resultant mixture was allowed to stand at 4° C. for 2 hours, followed by centrifugation at 7,000 r.p.m. for 15 minutes to collect a sediment. The thus-obtained sediment was dissolved in a small amount of a 20 mM tris-hydrochloric acid buffer and thoroughly dialyzed overnight at 4° C. against the same buffer. Precipitates formed during the dialysis were removed by centrifugation at 7,000 r.p.m. for 15 minutes to obtain 390 ml of a dialyzate.

(d) The thus-obtained dialyzate was adsorbed on DEAE-Toyopearl (φ5.5×19 cm) which had been equilibrated with a 20 mM tris-hydrochloric acid buffer (pH 7.4) and washed thoroughly with the same buffer. Using 4-liter portions of the same buffer which portions contained 0 to 0.3M of sodium chloride respectively, elution was then performed at a rate of 20 ml per fraction in accordance with the linear concentration gradient method. Active fractions were eluted around a sodium chloride concentration of approximately 0.15M, thereby obtaining 380 ml of active fractions.

(e) The resultant active factions were thoroughly dialyzed overnight at 4° C. against a 0.1M phosphate buffer (pH 7.0) and the dialyzate was caused to pass through a column ($\phi$2.5 cm×12 cm) of "Blue Sepharose" which had previously been equilibrated with the same buffer. Column effluent fractions (480 ml) which showed an absorption of $A_{280}$ were collected and then concentrated through a "DIAFLOW Membrane Filter YM-10".

(f) The concentrate obtained in the above procedure (e) was subjected to gel filtration using "Sephadex G-100" ($\phi$4.5×75 cm) and eluted at a rate of 8 ml per fraction with a physiological saline. Active fraction Nos. 88–104 were collected and concentrated by ultrafiltration to obtain 14.5 ml of PCI (protein weight: 136.1 mg, Lowry method).

Further, the yields of proteins obtained in the respective stages of purification will be described below.

| Step | | Protein weight (mg) |
| --- | --- | --- |
| Step (b) | (EDTA extraction) | 7226 |
| Step (c) | (Ammonium sulfate fractionation and dialysis) | 3184 |
| Step (d) | (DEAE-Toyopearl adsorption) | 531 |
| Step (e) | (Blue Sepharose adsorption) | 163 |
| Step (f) | (Sephadex G-100 adsorption) | 136 |

(2) Preparation of immunized spleen cells:

The above-purified PCI (100 µg) was emulsified in the Freund complete adjuvant and administered intra-peritoneally to BALB/c mice.

PCI (50 µg/administration) and an adjuvant emulsion were thereafter administered twice at an interval of 2 weeks and finally, 50 µg of PCI was administered solely to complete the immunization.

Three days later, the mice were sacrificed. After taking out their spleens and chopping same, they were filtered through a 100-mesh nylon mesh to obtain isolated spleen cells.

(3) Preparation of hybridoma:

A hypotonic solution (155 mM ammonium chloride) was added to the thus-obtained immunized spleen cells to subject red blood cells to hemolysis. The cells were then washed three times with Iscove's modified Dulbecco's medium (IMDM). On the other hand, mouse myeloma cells PAI were also washed three times with IMDM. Both cells were counted. The spleen cells and PAI cells were combined together at a ratio of 5:1, followed by centrifugation. The supernatant was decanted out, and after loosening and separating the resultant cell sediment thoroughly, 0.5 ml of a 45% solution obtained by diluting polyethylene glycol (PEG) 4,000 with a culture medium was added dropwise to effect fusion. After allowing the resultant mixture to stand at 37° C. for 30 seconds, 1 ml of IMDM was added gently over 1 minute. Thereafter, 10 ml of IMDM was added over 5 minutes to a final volume of 40 ml in a centrifugal tube. The resultant mixture was centrifuged at 1,000 rpm for 8 minutes.

The resulting sediment was suspended in IMDM which had been added with 10% of fetal calf serum (FCS). The suspension was centrifuged again and the resultant supernatant was decanted out.

The thus-obtained sediment was suspended again in 10% FCS-added IMDM in which $10^{-4}$M of hypo-xanthine, $4\times10^{-7}$M of aminopterin and $1.6\times10^{-5}$M of thymidine (HAT-) had been added in advance. The resultant suspension was poured in 100-µl portions into the individual wells of a 96-well microtiter plate. Each well was added with 50 µl of the medium every third–fourth day. Growth of cells was observed.

It was confirmed that hybridomas were only allowed to grow owing to the selective action of HAT.

(4) Screening of antibody-secreting hybridoma:

The culture in a well, in which hybridomas had grown, was collected and a test was performed by enzyme immunoassay to determine if PCI-antibody secreting hybridomas were contained there. First of all, PCI was poured at a rate of 0.1 µg/100 µl/well into each well of a 96-well microtiter plate ("Immunoplate I", product of NUNC Company). The microtiter plate was left over at 25° C. for 18 hours so as to adsorb PCI. Thereafter, a culture as a sample was poured at a rate of 100 µl/well to react at 25° C. for 2 hours. After washing the culture three times with a phosphate-buffered saline containing 0.05% of "Tween 20" (PBS-Tween), horse radish peroxidase conjugated goat anti-mouse IgG (product of KPL Laboratories, Inc.) was added at a rate of 100 µl/well and two hours later, the culture was washed three times with PBS-Tween. Each well was then added with a 0.1M citric acid-sodium hydroxide buffer (pH 4.0) containing 0.001% of hydrogen peroxide solution and 0.4 mg/ml of orthophenylene diamine (product of Sigma Chemical Company) and the absorbance of the culture in each well was measured at a wavelength of 492 nm.

Since development of a stain was observed only in wells where an antibody to PCI existed in the sample, cells were collected from the wells which were stained.

(5) Cloning of hybridomas which secrete a monoclonal antibody specific to PCI:

Abdominal cells collected by injecting IMDM into the abdominal cavity of a mouse were used as feeder cells.

The abdominal cells suspended at $1\times10^5$ cells/ml in 10% FCS-added IMDM were poured in 100-µl portions into the individual wells of a 96-well microtiter plate. On the following day, antibody-secreting hybridomas were prepared at a concentration of 5 cells/ml and poured in 100-µl portions into the individual wells. Every third day, the culture medium was replaced by a fresh supply of the same medium, and culture supernatants were successively sampled out from wells in which hybridomas had grown to an appropriate volume. Confirmation of the secretion of the antibody was conducted by the same method as that described above. The cultures of positive wells were cloned again to obtain hybridomas secreting an anti-PCI monoclonal antibody. Six types of hybridomas were obtained. They were named PCI-H39 (deposited under FERM BP-1701 with Fermentation Research Institute, Agency of Industrial Science and Technology, Ministry of International Trade and Industry, Japanese Government), PCI-H46 (FERM BP-1702), PCI-H167 (FERM BP-1703), PCI-H169 (FERM BP-1704), PCI-H176 (FERM BP-1705) and PCI-H180 (FERM BP-1706) in accordance with the types of the anti-PCI monoclonal antibodies which they secreted respectively.

(6) Preparation of anti-PCI monoclonal antibody:

Seven-weeks-old or still older BALB/c mice were intraperitoneally administered with 0.5 ml of pristane (product of Aldrich Chemical Co., Inc.). About one week later, the mice were intraperitoneally inoculated with the above-obtained hybridomas at a rate of $1\times10^6$ cells/mouse. About 10 days later, ascitic fluid was collected from the abdominal cavities of the mice. The fluid was centrifuged at 3,000 rpm for 10 minutes to collect a supernatant. Ammonium sulfate was added to 5 ml of the supernatant until the final concentration of ammonium sulfate reached 50% saturation. The resultant mixture was allowed to stand overnight at 4° C. The mixture was then centrifuged at 3,000 rpm for 15 minutes, and the resultant sediment was dissolved in a 0.1M tris-hydrochloric acid buffer (pH 8) and thereafter dialyzed against the same buffer. The resulting dialyzate was subjected to chromatography on a column packed with "Protein A Sepharose CL-4B" (product of Pharmacia AB) which had been equilibrated with the same buffer.

The elution of the monoclonal antibody was conducted with a 0.1M glycin-0.15M sodium chloride buffer (pH 2.7), whereby the anti-PCI monoclonal antibody was obtained. When PCI-H39 was used, 14.2 mg of PCI-A39 was obtained. 20.2 mg of PCI-A46 from PCI-H46, 22.9 mg of PCI-A167 from PCI-H167, 25.0 mg of PCI-A169 from PCI-H169, 25.0 mg of PCI-A176 from PCI-H176, and 8.6 mg of PCI-A180 from PCI-H180.

Example 1

Cloning of PCI cDNA (1) Screening of the human placental cDNA library:

(a) cDNA library:

The human placental cDNA library was a product of Clontech Laboratories, Inc. cDNA, which had been prepared from human placental mRNA of 1.8 kb on average by using a reverse transcriptase, was coupled to the EcoR I site of λgt11phage by way of an EcoR I linker. The library was a recombinant λgt11phage composed of an independent clone of $1.0 \times 10^6$ cells.

(b) Host *E. coli* cells Y1090 (ATCC 37197) were streaked on an LB agar plate (10 g Bacto-tryptone, 5 g Bacto-yeast extract, 5 g sodium chloride, 2 g maltose, 5 g agar, 1 l distilled water; pH 7.5) which contained ampicillin (100 µg/ml) and maltose, followed by overnight culture at 37° C. A single colony thus occurred was transplanted to an LB medium (10 g Bacto-tryptone, 5 g Bacto-yeast extract, 5 g sodium chloride, 5 g maltose, 1 l distilled water; pH 7.5) which contained ampicillin (100 µg/ml) and maltose, followed by overnight shaking culture at 37° C.

(c) Infection of the phage library:

An overnight culture (0.2 ml) of host *E. coli* Y1090 cells was mixed with 0.1 ml of the phage library which had been prepared to $3.7–5.5\times10^5$ pfu/ml with a λ diluent (10 mM tris-HCl buffer, 10 mM magnesium chloride; pH 7.5). The resultant mixture was stood for 20 minutes at room temperature to have the phage adsorbed on the host cells. After addition and mixing of 2.5 ml of an LB top layer agar medium (10 g Bacto-tryptone, 5 g Bacto-yeast extract, 5 g sodium chloride, 2 g maltose, 7.2 g agar, 1 l distilled water; pH 7.5) which contained maltose and had been maintained warm at 45° C., the resultant mixture was spread on an LB agar plate containing maltose and having a diameter of 9 cm and was then cultured at 42° C. for 3 hours and a half.

(d) Transfer to a nitrocellulose filter:

After the sterilized nitrocellulose filter was saturated with 10 mM of isopropyl-β-D thioglactopyranoside (IPTG), it was dried. The dried filter was then applied over the LB agar plate which had been cultured at 42° C. for 3 hours and a half and contained a λgt11 phage plaque occurred. After culturing at 37° C. for additional 3 hours and a half, the filter was peeled off. The plate with the phage plaque occurred was stored at 4° C. After washing the filter with TBST (10 mM tris-HCl buffer, 150 mM sodium chloride, 0.05% "Tween 20"; pH 8.0), the filter was subjected to blocking at room temperature for 30 minutes with 1% procine serum albumin/TBST.

(e) Binding of a primary antibody:

The filter was placed in a solution of the primary antibody and was reacted at room temperature for 30 minutes under gentle shaking. As the primary antibody, the anti-PCI mouse monoclonal antibody (obtained in Referential Example) dissolved in the TBST was employed after allowing the liquid mixture to stand at room temperature for 30 minutes and absorbing foreign antibodies. As an anti-PCI mouse monoclonal antibody liquid mixture, was employed that containing PCI-A39+PCI-A46+PCI-A180 (1:1:0.5), 1 mg/ml of bovine serum albumin and 0.25 µg/m–0.04 µg/ml of an *E. coli* extract (product of Promega Corporation).

After the reaction with the primary antibody, the filter was washed three times, for 10 minutes each, with TBST.

(f) Binding of a secondary antibody:

The filter was then transferred into a solution of the secondary antibody and reacted at room temperature for 30 minutes under gentle stirring. As the secondary antibody, it was used that obtained by diluting an alkaline phosphatase-conjugated anti-mouse IgG (H+L) (product of Promega Corporation) to a concentration of 1/7,500 of its original concentration with TBST.

The filter was then washed three times, for 10 minutes each, with TBST, followed by washing once with an AP buffer (100 mM tris-HCl buffer, 100 mM sodium chloride, 5 mM magnesium chloride; pH 9.5).

(g) Development of a color:

The filter was immersed in a color development substrate solution which had been obtained by mixing 33 µl of a nitroblue tetrazolium solution (50 mg/ml) and 66 µl of a solution of 5-bromo-4-chloro-3-indolyl phosphate (50 mg/ml).

After allowing a stain to develop at room temperature for 1 hour, the filter was transferred into a reaction terminating solution (20 mM tris-HCl buffer, 5 mM sodium ethylenediamine tetraacetate; pH 8.0) so as to terminate the stain development.

(h) Preparation and purification of positive plaques:

Plaques corresponding to positive spots where the development of a stain was observed were collected together with the agar medium and were then transferred into a 0.1 ml of a TMG buffer (10 mM tris-HCl buffer, 10 mM magnesium chloride, 100 µg/ml gelatin; pH 7.4). Two drops of chloroform were added, followed by centrifugation at 4° C. and 4,000 rpm for 15 minutes. One drop of chloroform was then added to the resultant supernatant and the thus-prepared mixture was stored at 4° C.

The above-described screening was conducted on about $3\times10^6$ phage plaques. As a result, 26 positive plaques were obtained.

With respect to five plaques which showed strong strain development, their phage solutions were separately diluted to a suitable extent and then subjected to screening twice to purify the phages.

(2) Preparation of recombinant phage DNA:

Host *E. coli* cells Y1088 (ATCC 337195) were infected with the thus-obtained 5 strains of recombinant phages, and the phages were induced to occur at 42° C. Following a preparation method of λ phage [Bernard Perbal, PREPARATION OF λ PHAGE DNA in A PRACTICAL GUIDE TO MOLECULAR CLONING, pp175–184, A Wiley-Interscience Publication (1984), New York, U.S.A.], a small-volume preparation and a large-volume preparation, both, by the plate method and a large-volume preparation by a liquid culturing method were conducted successively to obtain 10⁹ pfu/ml of recombinant phages.

In accordance with a λDNA preparation process [Bernard Perbal, PURIFICATION OF λ DNA in A PRACTICAL GUIDE TO MOLECULAR CLONING, pp184–187, A Wiley-Interscience Publication (1984), New York, U.S.A.], a phage solution which had been concentrated to 10¹¹ pfu/ml by the polyethylene glycol precipitation method was purified by ultra-centrifugation in 2 steps concentration of glycerol [Written by Bernard Perbal, translated by Shigeyasu Kobayashi: Practical Handbook of Gene Manipulation Experiments, pp175 (1985), The Jatec Publishing Co.].

Using the purified recombinant phage, recombinant phage DNA was also prepared in accordance with the preparation method of λDNA. About 30–160 μg of DNA was obtained from 300 ml of the culture.

(3) Subcloning of cDNA:

pUC118 (product of Takara Shuzo Co., Ltd.) was used as a vector. pUC118 was cleaved with EcoR I. The five strains of recombinant λgt11phage DNAs were separately ligated with the thus-cleaved pUC118 by using a DNA ligation kit (product of Takara Shuzo Co., Ltd.).

When recombinant vectors thus obtained were separately introduced in host *E. coli* cells MV1304 (product of Takara Shuzo Co., Ltd.), five types of recombinant vectors pMKT1, pMKT3, pMKT5, pMKT7 and pMKT9 corresponding respectively to the 5 strains of the recombinant λgt11phage DNAs were obtained from the resultant transformants of the host cells MV1304.

Restriction endonuclease maps were prepared by using various restriction endonucleases. All of the recombinant vectors commonly contained the cleaved regions of Pst I, Sac I, Sph I and Hind III. Each of the thus-inserted fragments had a length of about 1.5 kb. The restriction endonuclease map of pMKT7 having the longest fragment inserted is shown in FIG. 1. The length of pMKT7 was about 4.8 kb.

(4) Determination of the nucleotide sequence of PCI cDNA:

The resultant PCI cDNA recombinant vector was treated using various restriction endonucleases and exonuclease III—mungbeannuclease separately, so that the strand of cDNA was shortened. A short stranded plasmid was then reconstructed using pUC118 as a vector. Host *E. coli* cells MV1304 were then transformed with the short-stranded plasmid thus obtained. A culture of the resultant transformant was infected with the helper phage M13K08 (product of Takara Shuzo Co., Ltd.). From phage particles thus grown, a single-stranded DNA was prepared. Its nucleotide sequence was determined by the dideoxynucleotide chain termination method.

The nucleotide sequence is shown in FIG. 2 (SEQ ID NO:2). It was possible to obtain cDNA which had an almost complete length as long as 1567 (FIG. 2). It has been found that the 957 bp base sequence starting from the 4th base G and ending up with the 960th base C codes the sequence of the 319 amino acids of the polypeptide according to the present invention.

*E. coli* MV1304/pMKT7, which contains the plasmid coding whole open reading frame of the polypeptide of this invention, has been deposited under FERM BP-1262 with Fermentation Research Institute, Agency of Industrial Science and Technology, Ministry of International Trade and Industry, Japanese Government.

Example 2

Construction of Plasmid for Expression of PCI cDNA and Transformation of Host Cells with the Plasmid (1) Selection of an expression vector:

As illustrated in FIG. 2, the translation starting site ATG of PCI cDNA is located within the recognition region of the restriction endonuclease Nco I. The coding region for the peptide of this invention can therefore be easily expressed by ligating a DNA fragment with an expression vector which has the Nco I region in the downstream of a strong promotor.

Accordingly, it was decided to use an expression vector pKK233-2 which had the trc promotor, the strong promotor of *E. coli*, and the ribosome-binding site of LacZ as well as the translation starting site ATG downstream by eight bases of the ribosome-binding site [Amann, E. and Brosius, J., Gene, 40, 183–190 (1985)]. The translation starting site ATG of pKK233-2 is present in the recognition region of the restriction endonuclease Nco I.

Figure 3:
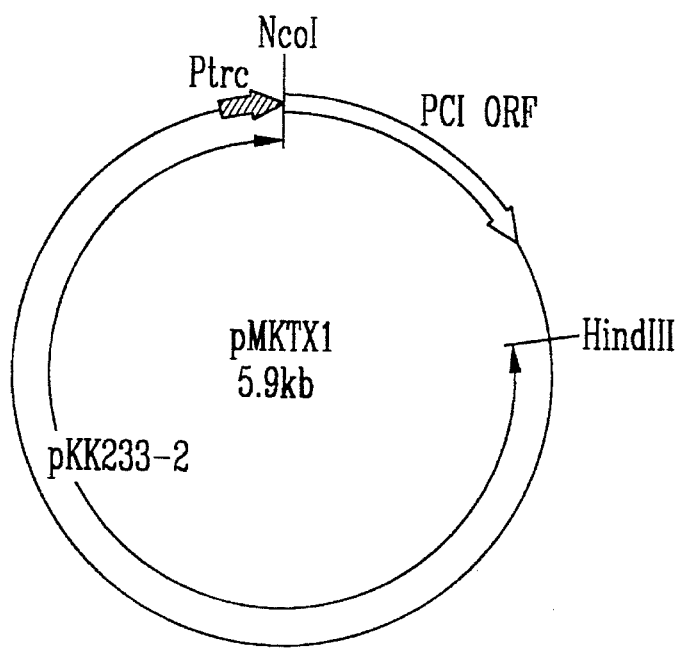
FIG. 3 is a sketch showing the restriction enzyme map of the plasmid pMKTX1 for expressing the polypeptide of this invention.

(2) Construction of a plasmid for expression of PCI cDNA:

The plasmid pMKT7 which had been prepared in Example 1 and contained PCI cDNA was cleaved with the restriction endonucleases Nco I and Hind III. A DNA fragment, which had a length of 1,308 (FIG. 2) bp and contained a region which codes the polypeptide of this invention, was isolated by low melting point agarose gel electrophoresis [Written by Bernard Perbal and translated under the supervision of Shigeyasu Kobayashi: "Idenshi Sosa Jikken Jitsuyo Handbook (Practical Handbook of Gene Manipulation Experiments), 211–212 (1985), The JATEC Publishing Co., Ltd.]. The vector pKK233-2, which had been cleaved by the restriction endonucleases Nco I and Hind III in advance, and the above DNA fragment were then ligated by using the DNA ligation kit (product of Takara Shuzo Co., Ltd.), whereby a plasmid pMKTX1 was constructed (FIG. 3).

(3) The plasmid pMKTX1 had been constructed by the above procedure (2) was introduced into competent cells of host *E. coli* JM105 [C. Yanisch-Perron, J. Vieira and J. Messing: Improved M13 Phage Cloning Vectors and Host Strains—Nucleotide Sequences of the M13mp18 and pUC19 Vectors, Gene, 33, 103–119 (1985)], which competent cells had been prepared in accordance with the method proposed by Wiestars and Simmanis [Hanahan, D.: DNA Cloning: A Practical Approach, Vol. 1, (D. M. Glover, ed.), pp121, (1985) IRL Press, Oxford]. Selection of a transformant *E. coli* JM105/pMKTX1 was effected on an LB agar plate (1% Bacto-tryptone, 0.5% Bacto-yeast extract, 1% sodium chloride, 1.5% agar) which contained 100 μg/ml of ampicillin.

The resultant transformant *E. coli* JM105/pMKTX1 has been deposited under FERM BP-1407 with Fermentation Research Institute, Agency of Industrial Science and Technology, Ministry of International Trade and Industry, Japanese Government.

Example 3

Confirmation of Expression of the Polypeptide of This Invention by the Western Blotting Technique

*E. coli* JM 105/pMKTX1 prepared in Example 2 was cultured overnight at 37° C. on an LB agar plate which contained 100 μg/ml of ampicillin. The resultant colony was inoculated to 50-ml portions of SOC medium (20 g Bacto-tryptone, 5 g Bacto-yeast extract, 10 mM sodium chloride, 2.5 mM potassium chloride, 10 mM magnesium chloride, 10 mM magnesium sulfate, 20 mM glucose, 50 µg/ml ampicillin, 1 l distilled water; pH 7.0), which portions were contained individually in 500-ml Erlenmeyer flasks. The transformant was cultured under shaking at 37° C. for 2 hours. Isopropyl-β-D-thiogalactopyranoside was added to a final concentration of 1 mM, followed by culture under shaking for additional 2 hours. Subsequent to collection of cells, they were suspended in 0.2 ml of TBS (10 mM tris-HCl buffer, 150 mM sodium chloride; pH 8.0). Lysozyme, ribonuclease and deoxyribonuclease were then added to at a rate of 100 µg/ml each. The resultant suspension was caused to freeze in dry ice/ethanol, followed by thawing. This freezing and thawing procedure was repeated again, and the suspension was then allowed to stand at room temperature for 15 minutes. EDTA was added to a final concentration of 20 mM, thereby obtaining a lysate. A centrifugal supernatant of the lysate was allowed to pass through a "Millipore" filter, so that an extract of *E. coli* JM 105/pMKTX1 was obtained.

Figure 4:
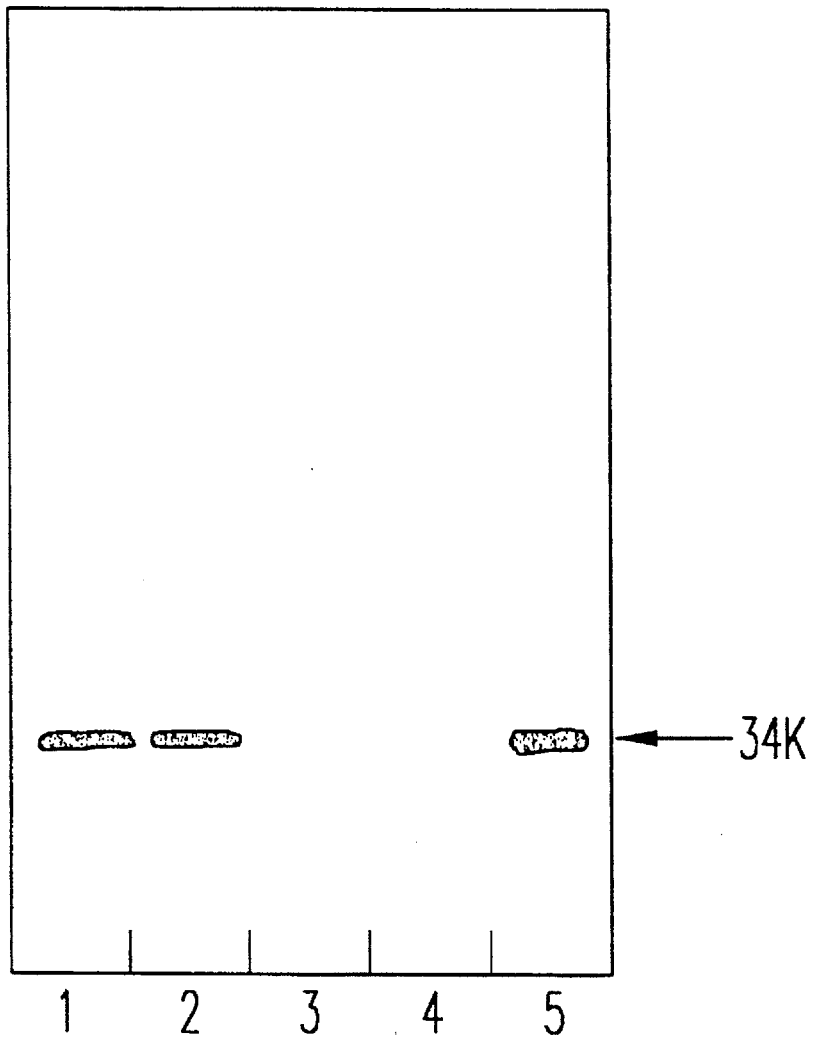
FIG. 4 diagrammatically depicts the results of western blotting of the polypeptide of this invention upon its SDS polyacrylamide gel (10% gel) electrophoresis, in which Lane 1 was obtained by the electrophoresis of the cell extract of E. coli JM105/pMKTX1 cultured in the presence of IPTG added, Lane 2 was recorded by the electrophoresis of the cell extract of E. coli JM105/pMKTX1 cultured without addition of IPTG, Lane 3 was resulted by the electrophoresis of the cell extract of E. coli JM105/pKK233-2 cultured in the presence of IPTG added, Lane 4 was obtained by the electrophoresis of the cell extract of E. coli JM105/pKK233-2 cultured without addition of IPTG, and Lane 5 was formed by the electrophoresis of PCI.

After reducing 15 µl of the thus-obtained extract with β-mercaptoethanol, it was subjected to SDS polyacrylamide electrophoresis (10% gel). Western blotting was conducted using anti-human placentaderived PCI monoclonal antibody PCI-A46 and a protoblot immunoassay system (product of Promega Biotec Corp.). As a result, the expression of the polypeptide of this invention having a molecular weight substantially equivalent to PCI derived from the human placenta was confirmed (FIG. 4).

Example 4

Production of Polypeptide of This Invention (1) Culture:

The transformant *E. coli* JM105/pMKTX1 was cultured overnight at 37° C. on an LB agar plate which contained 100 µg/ml of ampicillin. The resultant colony was inoculated respectively to four 5-ml portions of an LB medium (which had been obtained by omitting agar from an LB agar medium) containing 50 µg/ml of ampicillin. The four 5-ml portions were contained in L-shaped tubes respectively. Subsequent to overnight culture at 37° C. under shaking, 0.5-ml portions of each culture were separately inoculated to forty 50-ml portions of an MMCA medium (10.5 g dipotassium phosphate, 4.5 g potassium phosphate, 1.0 g ammonium sulfate, 0.5 g sodium citrate, 0.2 g magnesium sulfate, 2.0 g glucose, 5.0 µl thiamine hydrochloride, 5.0 g Casamino acid, 50 µg/ml of ampicillin, 1 l distilled water; pH 7.0). The forty 50-ml portions were contained in 500-ml Erlenmeyer flasks respectively. After culturing the transformant at 37° C. for 4 hours under shaking, Isopropyl-β-D thiogalactopyranoside was added to a final concentration of 1 mM, followed by culture under shaking for additional 2.5 hours.

(2) Extraction and purification:

(a) After harvesting the cells, they were suspended in 50 ml of a 25 mM tris-HCl buffer (pH 7.4) which contained 25 mM of EDTA. The suspension was centrifuged to obtain washed cells. The washed cells were suspended in 75 ml of the same buffer and subsequent to freezing and thawing, a supernatant was obtained by centrifugation. The residue was suspended again in 75 ml of the same buffer and after freezing and thawing, an additional supernatant was obtained by centrifugation. Both supernatants were combined and impurities were removed therefrom with an aqueous ammonium sulfate solution of 30% saturation. The resultant solution was dialyzed against a 25 mM tris-HCl buffer (pH 7.4) to obtain 244 ml of an *E. coli* extract.

Figure 5:
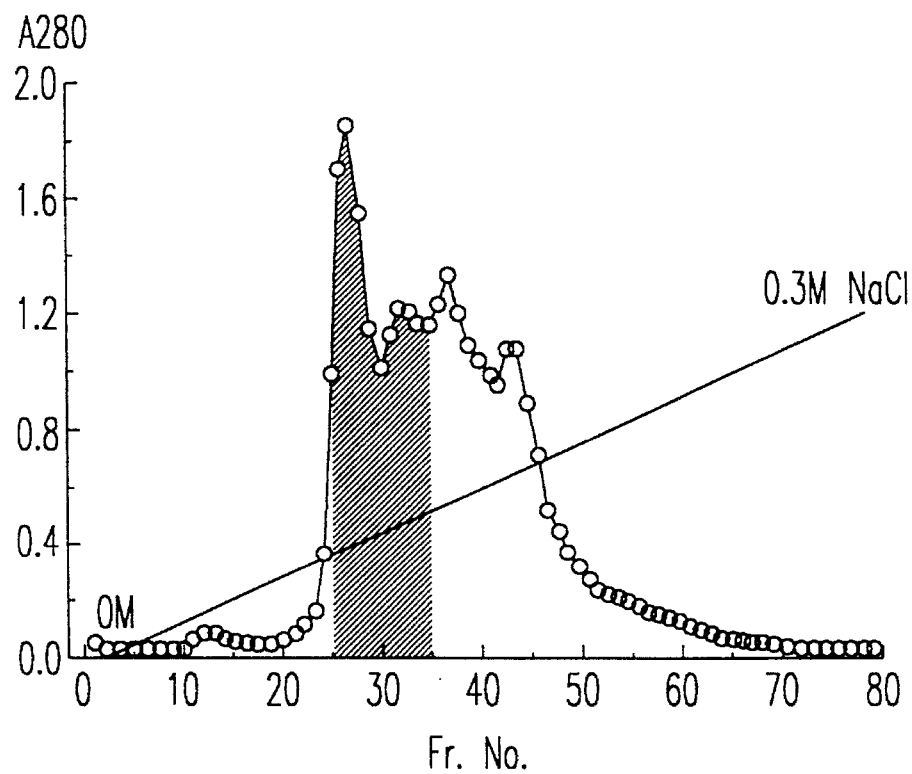
FIG. 5 is a graph showing the elution of the E. coli extract from the DEAE-Toyopearl column by the linear NaCl gradient method in Example 4, in which the shaded fractions were collected.

(b) The *E. coli* extract obtained in the above procedure (a) was caused to adsorb on a DEAE-Toyopearl column ($\phi$1.6× 10 cm) which had been equilibrated with a 50 mM tris-HCl buffer (pH 7.4). The column was washed thoroughly with the same buffer. Using 240 ml of the same buffer whose portions contained 0 to 0.3M of sodium chloride respectively, elution was then performed at a rate of 3 ml per fraction in accordance with the linear concentration gradient method so that fractions containing the polypeptide of this invention were obtained in a total volume of 39 ml (FIG. 5). Incidentally, the amount of the polypeptide of this invention in each fraction was determined by ELISA (Enzyme-Linked Immunosorbent Assay).

Figure 6:
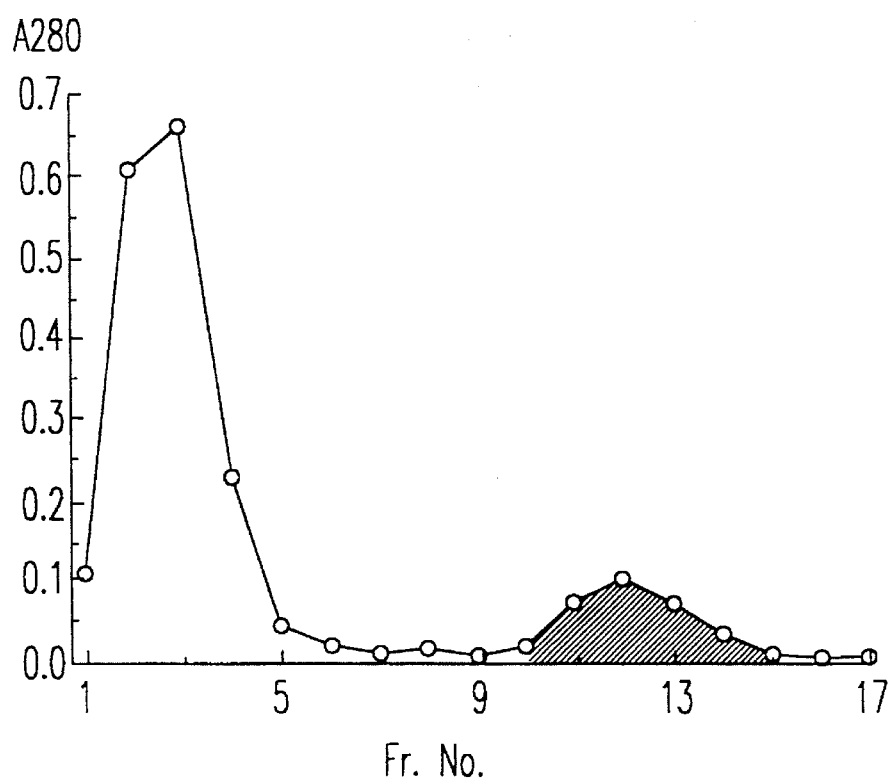
FIG. 6 is a graph showing the elution of the peptide of this invention from the antibody column in Example 4, in which the shaded fractions were collected.

(c) Fractions containing the polypeptide of this invention, which had been obtained in the above procedure (b), were charged into an antibody column ($\phi$3×4 cm) in which the monoclonal antibody PCI-A46 was bound on cyanogen bromide activated "Sepharose 4B". After washing the column thoroughly with a 0.1M tris-HCl buffer (pH 7.4) containing 0.5M of sodium chloride, elution was performed at a rate of 2 ml per fraction with 50 ml of a 0.1M sodium acetate buffer (pH 5.0) which contained 0.5M of sodium chloride, whereby fractions containing the polypeptide of this invention were obtained in a total volume of 20 ml (FIG. 6). Those fractions were concentrated by "Immersible CX-10" (product of Millipore Corporation) and then dialyzed against a 25 mM tris-HCl buffer (pH 7.4) containing 0.15M of sodium chloride, thereby obtaining 3.75 ml of a polypeptide sample of this invention in a pure form (protein weight: 4.7 mg—determined by BIO-RAD PROTEIN ASSAY). Since the thus-obtained polypeptide of this invention showed a single band in its SDS-polyacrylamide gel electrophoresis, it is believed to consist of a single ingredient free of any impurities.

Further, the yields of proteins obtained in the respective stages of purification will be described below.

| Step | | Protein weight (mg) |
| --- | --- | --- |
| Step (a) | (*E. coli* extract) | 95.2 |
| Step (b) | (DEAE-Toyopearl adsorption) | 21.5 |
| Step (c) | (Antibody column adsorption) | 4.7 |

Example 5

Properties of Polypeptide of This Invention (1) Determination of the amino acid sequence of the N-terminal:

Subsequent of dialysis of 2 mg of the polypeptide of this invention against distilled water, it was lyophilized. Using JEOL JAS-570K Sequence Analyzer, it was converted into PTH amino acid and analyzed. Results of the analysis are shown in the following table.

| Cycle No. | Amino acid | nmol |
| --- | --- | --- |
| 1 | Ala | 13.4 |
| 2 | Gln | 12.6 |
| 3 | Val | 11.7 |
| 4 | Leu | 13.5 |
| 5 | Arg | 12.4 |
| 6 | Gly | 8.9 |
| 7 | Thr | n.d.* |
| 8 | Val | 9.5 |

| Cycle No. | Amino acid | nmol |
|---|---|---|
| 9 | Thr | n.d.* |
| 10 | Asp | 11.1 |

*n.d.: Not detected.

From the above results, the amino acid sequence of the N-terminal of the polypeptide of this invention has been determined as follows:

Ala-Gln-Val-Leu-Arg-Gly-Thr-Val-Thr-Asp- (2) Measurement of the molecular weight:

After reducing the polypeptide of this invention with 2-mercaptoethanol, its molecular weight was measured by 12.5% SDS-polyacrylamide gel electrophoresis in accordance with the method proposed by Laemmli [Laemmli, U.K.: Nature, 227, 680–685 (1970)]. Employed as molecular weight markers were phosphorylase b (m.w. 94,000), bovine serum albumin (m.w. 67,000), egg white albumin (m.w. 43,000), carbonic anhydrase (m.w. 30,000), soybean trypsin inhibitor (m.w. 20,100) and α-lactoalbumin (m.w. 14,400).

The molecular weight of the polypeptide of this invention was calculated as 34,000±1,000.

(3) Measurement of the isoelectric point:

Using "AMPHOLINE PAGPLATE" (trade mark; pH 3.5–9.5; product of LKB), the isoelectric point was measured by polyacrylamide gel isoelectric focusing in accordance with the method proposed by Wrigley [Wrigley, C. W.: Methods Enzymol., 21, 559–564 (1971)].

The isoelectric point of the polypeptide of this invention was calculated to be 5.0±0.1.

(4) Determination of stability:

The stability of the polypeptide of this invention in plasma was determined.

Mixed were 5 µl portions of the polypeptide (60 µg/ml) of this invention with 100 µl portions of human plasma. The resultant mixtures were incubated at 37° C. separately for different time periods ranging from 0 minute to 30 minutes. Each of the mixtures was then added with 200 µl of 0.0125M calcium chloride to measure any prolongation of the coagulation time in accordance with the recalcification method. Measurement results are shown in the following table, in which the respective degrees of prolongation will be expressed in terms of percentage of prolonged coagulation time by assuming that the coagulation time be 100% when the polypeptide of this invention was not added.

| Incubation time (minutes) | 0 | 0 | 20 | 30 |
|---|---|---|---|---|
| Percent prolongation of coagulation time (n=2) (%) | 223 | 220 | 209 | 200 |

The polypeptide of this invention remained stable for 30 minutes at 37° C. in the plasma.

(5) Determination of anticoagulant activities:

(i) Measurement of recalcification time:

In a small silicone-treated glass test tube, 100 µl of a solution containing the polypeptide of this invention and 100 µl of standard human plasma were mixed. After allowing the resultant mixture to stand at 37° C. for 3 minutes, 100 µl of a 0.025M aqueous solution of calcium chloride was added. They were mixed well and the time was measured until the blood was coagulated.

In the following table, measurement results will be shown in terms of percent prolongation of coagulation time by assuming that the coagulation time was 100% when the polypeptide of this invention was not added.

| Amount of polypeptide of this invention added (µg/ml) | 0 | 1 |
|---|---|---|
| Percent prolongation of coagulation time (n=2) (%) | 100 | 137 | ii) Measurement of prothrombin time:

Mixed in a glass cuvette were 50 µl of a solution containing the polypeptide of this invention, 50 µl of a 20 mM tris-HCl buffer (pH 7.4) containing 0.15M of sodium chloride and 0.5% of human serum albumin, and 100 µl of thromboplastin ("Lyoplastin", trade mark; product of Mochida Pharmaceutical Co, Ltd.) which had been diluted to a concentration of 0.1 mg/ml with a 20 mM aqueous solution of calcium chloride. After allowing the resultant mixture to stand at 37° C. for 3 minutes, was added 200 µl of standard human plasma which had been diluted twofold with a 0.15M saline. The coagulation time was then measured using "COAGTEC TE-600" (trade name; product of Erma Inc., Tokyo).

In the following table, measurement results will be shown in terms of percent prolongation of coagulation time by assuming that the coagulation time was 100% when the polypeptide of this invention was not added.

| Amount of polypeptide of this invention added (µg/ml) | 0 | 12.5 | 25 | 50 | 100 |
|---|---|---|---|---|---|
| Percent prolongation of coagulation time (n=2) (%) | 100 | 132 | 184 | 284 | 380 | iii) Measurement of activated partial thromboplastin time:

Mixed in a glass cuvette were 50 µl of a solution containing the polypeptide of this invention and 50 µl of "ACTIVATED THROMBOFAX" (trade name; product of Ortho Pharmaceutical Corp.). After allowing the resultant mixture to stand at 37° C. for 2 minutes, 100 µl of human plasma was added. The thus-obtained mixture was left over for 4 minutes. After addition of 200 µl of a 0.0125M solution of calcium chloride, the coagulation time was measured using "COAGTEC TE-600" (trade name; product of Erma Inc., Tokyo).

In the following table, measurement results will be shown in terms of percent prolongation of coagulation time by assuming that the coagulation time was 100% when the polypeptide of this invention was not added.

| Amount of polypeptide of this invention added (µg/ml) | 0 | 50 | 100 | 150 |
|---|---|---|---|---|
| Percent prolongation of coagulation time (n=2) (%) | 100 | 107 | 120 | 141 |
| Amount of polypeptide of this invention added (µg/ml) | 200 | 300 | 500 | |
| Percent prolongation of coagulation time (n=2) (%) | 184 | 396 | 608 | |

Example 9

Comparison in Anticoagulant Activities Between the Polypeptide of This Invention and PCI The anticoagulant activities of the polypeptide of this invention were compared with those of PCI derived from the human placenta. 100-µl portions of each sample, said portions having different concentrations, were each mixed with 100 µl of a 0.5 mg/ml PT reagent ("Lyoplastin", trade mark;

product of Mochida Pharmaceutical Co., Ltd.). Three minutes later, 200 μl of standard plasma which had been diluted twofold with a physiological saline was added to measure the coagulation time.

As will be shown in Table 1, the polypeptide of this invention and PCI derived from the human placenta exhibited substantially the same coagulation time (PT) prolonging effects.

TABLE 1

Anticoagulant Activities of Invention Polypeptide and Human Placenta Derived PCI

| Sample added (μg/reaction mixture) | Coagulation time (seconds) | |
| --- | --- | --- |
| | Invention polypeptide | Human placenta derived PCI |
| 0 | 28 | 29 |
| 1 | 89 | 79 |
| 2 | 121 | 119 |
| 5 | 169 | 165 |
| 7 | 188 | 192 |

Example 7

Preparation into Dosage Form:

| Polypeptide of this invention | 1 mg |
| --- | --- |
| Albumin | 5 mg |
| Mannitol | 25 mg |
| Sodium chloride | 1.95 mg |
| Sodium phosphate | 3.85 mg |

The above ingredients were dissolved in 2 ml of distilled water for injection. The thus-prepared solution was filled in a sterilized vial, and was frozen provisionally at −30° C. to −40° C. for 2 hours. It was thereafter subjected to primary drying at −30° C. to +20° C. and 0.05 to 0.1 Torr for 35 hours and then to secondary drying at 30° C. and 0.01 to 0.05 Torr for 5 hours, thereby producing a vial for injection.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 319 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:1:

```
Ala  Gln  Val  Leu  Arg  Gly  Thr  Val  Thr  Asp  Phe  Pro  Gly  Phe  Asp  Glu
  1              5                        10                            15
Arg  Ala  Asp  Ala  Glu  Thr  Leu  Arg  Lys  Ala  Met  Lys  Gly  Leu  Gly  Thr
               20                        25                       30
Asp  Glu  Glu  Ser  Ile  Leu  Thr  Leu  Leu  Thr  Ser  Arg  Ser  Asn  Ala  Gln
          35                        40                  45
Arg  Gln  Glu  Ile  Ser  Ala  Ala  Phe  Lys  Thr  Leu  Phe  Gly  Arg  Asp  Leu
     50                  55                       60
Leu  Asp  Asp  Leu  Lys  Ser  Glu  Leu  Thr  Gly  Lys  Phe  Glu  Lys  Leu  Ile
 65                       70                       75                        80
Val  Ala  Leu  Met  Lys  Pro  Ser  Arg  Leu  Tyr  Asp  Ala  Tyr  Glu  Leu  Lys
               85                       90                            95
His  Ala  Leu  Lys  Gly  Ala  Gly  Thr  Asn  Glu  Lys  Val  Leu  Thr  Glu  Ile
              100                      105                      110
Ile  Ala  Ser  Arg  Thr  Pro  Glu  Glu  Leu  Arg  Ala  Ile  Lys  Gln  Val  Tyr
              115                      120                 125
Glu  Glu  Glu  Tyr  Gly  Ser  Ser  Leu  Glu  Asp  Asp  Val  Val  Gly  Asp  Thr
         130                      135                 140
Ser  Gly  Tyr  Tyr  Gln  Arg  Met  Leu  Val  Val  Leu  Leu  Gln  Ala  Asn  Arg
145                           150                      155                     160
Asp  Pro  Asp  Ala  Gly  Ile  Asp  Glu  Ala  Gln  Val  Glu  Gln  Asp  Ala  Gln
                         165                      170                      175
```

```
Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
            195                 200                 205

Phe Asp Lys Tyr Met Thr Ile Ser Gly Phe Gln Ile Glu Glu Thr Ile
            210                 215                 220

Asp Arg Glu Thr Ser Gly Asn Leu Glu Gln Leu Leu Leu Ala Val Val
225                     230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
            275                 280                 285

Lys Asn Phe Ala Thr Ser Leu Tyr Ser Met Ile Lys Gly Asp Thr Ser
            290                 295                 300

Gly Asp Tyr Lys Lys Ala Leu Leu Leu Leu Cys Gly Glu Asp Asp
305                     310                 315
```

( 2 ) INFORMATION FOR SEQ ID NO:2:

( i ) SEQUENCE CHARACTERISTICS:
        ( A ) LENGTH: 1567 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 136..1095

( x i ) SEQUENCE DESCRIPTION: SEQ ID NO:2:

```
GGATCCTTCA GCGTCTGCAT CTCGGCGTCG CCCCGCGTAC CGTCGCCCGG CTCTCCGCCG        60

CTCTCCCGGG GTTTCGGGGC ACTTGGGTCC CACAGTCTGG TCCTGCTTCA CCTTCCCCTG       120

ACCTGAGTAG TCGCC ATG GCA CAG GTT CTC AGA GGC ACT GTG ACT GAC TTC        171
                Met Ala Gln Val Leu Arg Gly Thr Val Thr Asp Phe
                 1               5                      10

CCT GGA TTT GAT GAG CGG GCT GAT GCA GAA ACT CTT CGG AAG GCT ATG        219
Pro Gly Phe Asp Glu Arg Ala Asp Ala Glu Thr Leu Arg Lys Ala Met
        15                  20                  25

AAA GGC TTG GGC ACA GAT GAG GAG AGC ATC CTG ACT CTG TTG ACA TCC        267
Lys Gly Leu Gly Thr Asp Glu Glu Ser Ile Leu Thr Leu Leu Thr Ser
30                  35                  40

CGA AGT AAT GCT CAG CGC CAG GAA ATC TCT GCA GCT TTT AAG ACT CTG        315
Arg Ser Asn Ala Gln Arg Gln Glu Ile Ser Ala Ala Phe Lys Thr Leu
45                  50                  55                  60

TTT GGC AGG GAT CTT CTG GAT GAC CTG AAA TCA GAA CTA ACT GGA AAA        363
Phe Gly Arg Asp Leu Leu Asp Asp Leu Lys Ser Glu Leu Thr Gly Lys
            65                  70                  75

TTT GAA AAA TTA ATT GTG GCT CTG ATG AAA CCC TCT CGG CTT TAT GAT        411
Phe Glu Lys Leu Ile Val Ala Leu Met Lys Pro Ser Arg Leu Tyr Asp
            80                  85                  90

GCT TAT GAA CTG AAA CAT GCC TTG AAG GGA GCT GGA ACA AAT GAA AAA        459
Ala Tyr Glu Leu Lys His Ala Leu Lys Gly Ala Gly Thr Asn Glu Lys
        95                  100                 105

GTA CTG ACA GAA ATT ATT GCT TCA AGG ACA CCT GAA GAA CTG AGA GCC        507
Val Leu Thr Glu Ile Ile Ala Ser Arg Thr Pro Glu Glu Leu Arg Ala
110                 115                 120
```

| | | | | | | | | | | | | | | | | |
|---|---|---|---|---|---|---|---|---|---|---|---|---|---|---|---|---|
| ATC | AAA | CAA | GTT | TAT | GAA | GAA | GAA | TAT | GGC | TCA | AGC | CTG | GAA | GAT | GAC | 555 |
| Ile | Lys | Gln | Val | Tyr | Glu | Glu | Glu | Tyr | Gly | Ser | Ser | Leu | Glu | Asp | Asp | |
| 125 | | | | 130 | | | | | 135 | | | | | | 140 | |
| GTG | GTG | GGG | GAC | ACT | TCA | GGG | TAC | TAC | CAG | CGG | ATG | TTG | GTG | GTT | CTC | 603 |
| Val | Val | Gly | Asp | Thr | Ser | Gly | Tyr | Tyr | Gln | Arg | Met | Leu | Val | Val | Leu | |
| | | | | 145 | | | | | 150 | | | | | 155 | | |
| CTT | CAG | GCT | AAC | AGA | GAC | CCT | GAT | GCT | GGA | ATT | GAT | GAA | GCT | CAA | GTT | 651 |
| Leu | Gln | Ala | Asn | Arg | Asp | Pro | Asp | Ala | Gly | Ile | Asp | Glu | Ala | Gln | Val | |
| | | | 160 | | | | | 165 | | | | | 170 | | | |
| GAA | CAA | GAT | GCT | CAG | GCT | TTA | TTT | CAG | GCT | GGA | GAA | CTT | AAA | TGG | GGG | 699 |
| Glu | Gln | Asp | Ala | Gln | Ala | Leu | Phe | Gln | Ala | Gly | Glu | Leu | Lys | Trp | Gly | |
| | | 175 | | | | | 180 | | | | | 185 | | | | |
| ACA | GAT | GAA | GAA | AAG | TTT | ATC | ACC | ATC | TTT | GGA | ACA | CGA | AGT | GTG | TCT | 747 |
| Thr | Asp | Glu | Glu | Lys | Phe | Ile | Thr | Ile | Phe | Gly | Thr | Arg | Ser | Val | Ser | |
| | | 190 | | | | | 195 | | | | | 200 | | | | |
| CAT | TTG | AGA | AAG | GTG | TTT | GAC | AAG | TAC | ATG | ACT | ATA | TCA | GGA | TTT | CAA | 795 |
| His | Leu | Arg | Lys | Val | Phe | Asp | Lys | Tyr | Met | Thr | Ile | Ser | Gly | Phe | Gln | |
| 205 | | | | | 210 | | | | | 215 | | | | | 220 | |
| ATT | GAG | GAA | ACC | ATT | GAC | CGC | GAG | ACT | TCT | GGC | AAT | TTA | GAG | CAA | CTA | 843 |
| Ile | Glu | Glu | Thr | Ile | Asp | Arg | Glu | Thr | Ser | Gly | Asn | Leu | Glu | Gln | Leu | |
| | | | | 225 | | | | | 230 | | | | | 235 | | |
| CTC | CTT | GCT | GTT | GTG | AAA | TCT | ATT | CGA | AGT | ATA | CCT | GCC | TAC | CTT | GCA | 891 |
| Leu | Leu | Ala | Val | Val | Lys | Ser | Ile | Arg | Ser | Ile | Pro | Ala | Tyr | Leu | Ala | |
| | | | 240 | | | | | 245 | | | | | 250 | | | |
| GAG | ACC | CTC | TAT | TAT | GCT | ATG | AAG | GGA | GCT | GGG | ACA | GAT | GAT | CAT | ACC | 939 |
| Glu | Thr | Leu | Tyr | Tyr | Ala | Met | Lys | Gly | Ala | Gly | Thr | Asp | Asp | His | Thr | |
| | | 255 | | | | | 260 | | | | | 265 | | | | |
| CTC | ATC | AGA | GTC | ATG | GTT | TCC | AGG | AGT | GAG | ATT | GAT | CTG | TTT | AAC | ATC | 987 |
| Leu | Ile | Arg | Val | Met | Val | Ser | Arg | Ser | Glu | Ile | Asp | Leu | Phe | Asn | Ile | |
| | | 270 | | | | | 275 | | | | | 280 | | | | |
| AGG | AAG | GAG | TTT | AGG | AAG | AAT | TTT | GCC | ACC | TCT | CTT | TAT | TCC | ATG | ATT | 1035 |
| Arg | Lys | Glu | Phe | Arg | Lys | Asn | Phe | Ala | Thr | Ser | Leu | Tyr | Ser | Met | Ile | |
| 285 | | | | | 290 | | | | | 295 | | | | | 300 | |
| AAG | GGA | GAT | ACA | TCT | GGG | GAC | TAT | AAG | AAA | GCT | CTT | CTG | CTG | CTC | TGT | 1083 |
| Lys | Gly | Asp | Thr | Ser | Gly | Asp | Tyr | Lys | Lys | Ala | Leu | Leu | Leu | Leu | Cys | |
| | | | | 305 | | | | | 310 | | | | | 315 | | |
| GGA | GAA | GAT | GAC | TAACGTGTCA | CGGGGAAGAG | CTCCCTGCTG | TGTGCCTGCA | | | | | | | | | 1135 |
| Gly | Glu | Asp | Asp | | | | | | | | | | | | | |
| | | | 320 | | | | | | | | | | | | | |

| | | |
|---|---|---|
| CCACCCCACT GCCTTCCTTC AGCACCTTTA GCTGCATTTG TATGCCAGTG CTTAACACAT | | 1195 |
| TGCCTTATTC ATACTAGCAT GCTCATGACC AACACATACA CGTCATAGAA GAAAATAGTG | | 1255 |
| GTGCTTCTTT CTGATCTCTA GTGGAGATCT CTTTGACTGC TGTAGTACTA AAGTGTACTT | | 1315 |
| AATGTTACTA AGTTAATGC CTGGCCATTT TCCATTTATA TATATTTTTT AAGAGGCTAG | | 1375 |
| AGTGCTTTTA GCCTTTTTTA AAAACTCCAT TTATATTACA TTTGTAACCA TGATACTTTA | | 1435 |
| ATCAGAAGCT TAGCCTTGAA ATTGTGAACT CTTGGAAATG TTATTAGTGA AGTTCGCAAC | | 1495 |
| TAAACTAAAC CTGTAAAATT ATGATGATTG TATTCAAAAG ATTAATGAAA AATAAACATT | | 1555 |
| TCTGTCCCCC TG | | 1567 |

( 2 ) INFORMATION FOR SEQ ID NO:3:

( i ) SEQUENCE CHARACTERISTICS:
  ( A ) LENGTH: 320 amino acids
  ( B ) TYPE: amino acid
  ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met | Ala | Gln | Val | Leu | Arg | Gly | Thr | Val | Thr | Asp | Phe | Pro | Gly | Phe | Asp |
| 1 | | | | 5 | | | | | 10 | | | | | 15 | |
| Glu | Arg | Ala | Asp | Ala | Glu | Thr | Leu | Arg | Lys | Ala | Met | Lys | Gly | Leu | Gly |
| | | | 20 | | | | | 25 | | | | | 30 | | |
| Thr | Asp | Glu | Glu | Ser | Ile | Leu | Thr | Leu | Leu | Thr | Ser | Arg | Ser | Asn | Ala |
| | | 35 | | | | | 40 | | | | | 45 | | | |
| Gln | Arg | Gln | Glu | Ile | Ser | Ala | Ala | Phe | Lys | Thr | Leu | Phe | Gly | Arg | Asp |
| | | 50 | | | | | 55 | | | | | 60 | | | |
| Leu | Leu | Asp | Asp | Leu | Lys | Ser | Glu | Leu | Thr | Gly | Lys | Phe | Glu | Lys | Leu |
| 65 | | | | | 70 | | | | | 75 | | | | | 80 |
| Ile | Val | Ala | Leu | Met | Lys | Pro | Ser | Arg | Leu | Tyr | Asp | Ala | Tyr | Glu | Leu |
| | | | | 85 | | | | | 90 | | | | | 95 | |
| Lys | His | Ala | Leu | Lys | Gly | Ala | Gly | Thr | Asn | Glu | Lys | Val | Leu | Thr | Glu |
| | | | 100 | | | | | 105 | | | | | 110 | | |
| Ile | Ile | Ala | Ser | Arg | Thr | Pro | Glu | Glu | Leu | Arg | Ala | Ile | Lys | Gln | Val |
| | | | 115 | | | | | 120 | | | | | 125 | | |
| Tyr | Glu | Glu | Glu | Tyr | Gly | Ser | Ser | Leu | Glu | Asp | Asp | Val | Val | Gly | Asp |
| | | 130 | | | | | 135 | | | | | 140 | | | |
| Thr | Ser | Gly | Tyr | Tyr | Gln | Arg | Met | Leu | Val | Val | Leu | Leu | Gln | Ala | Asn |
| 145 | | | | | 150 | | | | | 155 | | | | | 160 |
| Arg | Asp | Pro | Asp | Ala | Gly | Ile | Asp | Glu | Ala | Gln | Val | Glu | Gln | Asp | Ala |
| | | | 165 | | | | | 170 | | | | | 175 | | |
| Gln | Ala | Leu | Phe | Gln | Ala | Gly | Glu | Leu | Lys | Trp | Gly | Thr | Asp | Glu | Glu |
| | | | 180 | | | | | 185 | | | | | 190 | | |
| Lys | Phe | Ile | Thr | Ile | Phe | Gly | Thr | Arg | Ser | Val | Ser | His | Leu | Arg | Lys |
| | | | 195 | | | | | 200 | | | | | 205 | | |
| Val | Phe | Asp | Lys | Tyr | Met | Thr | Ile | Ser | Gly | Phe | Gln | Ile | Glu | Glu | Thr |
| | | 210 | | | | | 215 | | | | | 220 | | | |
| Ile | Asp | Arg | Glu | Thr | Ser | Gly | Asn | Leu | Glu | Gln | Leu | Leu | Leu | Ala | Val |
| 225 | | | | | 230 | | | | | 235 | | | | | 240 |
| Val | Lys | Ser | Ile | Arg | Ser | Ile | Pro | Ala | Tyr | Leu | Ala | Glu | Thr | Leu | Tyr |
| | | | | 245 | | | | | 250 | | | | | 255 | |
| Tyr | Ala | Met | Lys | Gly | Ala | Gly | Thr | Asp | Asp | His | Thr | Leu | Ile | Arg | Val |
| | | | 260 | | | | | 265 | | | | | 270 | | |
| Met | Val | Ser | Arg | Ser | Glu | Ile | Asp | Leu | Phe | Asn | Ile | Arg | Lys | Glu | Phe |
| | | 275 | | | | | 280 | | | | | 285 | | | |
| Arg | Lys | Asn | Phe | Ala | Thr | Ser | Leu | Tyr | Ser | Met | Ile | Lys | Gly | Asp | Thr |
| | 290 | | | | | 295 | | | | | 300 | | | | |
| Ser | Gly | Asp | Tyr | Lys | Lys | Ala | Leu | Leu | Leu | Leu | Cys | Gly | Glu | Asp | Asp |
| 305 | | | | | 310 | | | | | 315 | | | | | 320 |

(2) INFORMATION FOR SEQ ID NO:4:

(i) SEQUENCE CHARACTERISTICS:
        (A) LENGTH: 957 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:4:

```
GCACAGGTTC  TCAGAGGCAC  TGTGACTGAC  TTCCCTGGAT  TTGATGAGCG  GGCTGATGCA      60
GAAACTCTTC  GGAAGGCTAT  GAAAGGCTTG  GGCACAGATG  AGGAGAGCAT  CCTGACTCTG     120
TTGACATCCC  GAAGTAATGC  TCAGCGCCAG  GAAATCTCTG  CAGCTTTTAA  GACTCTGTTT     180
```

-continued

```
GGCAGGGATC  TTCTGGATGA  CCTGAAATCA  GAACTAACTG  GAAAATTTGA  AAAATTAATT     240

GTGGCTCTGA  TGAAACCCTC  TCGGCTTTAT  GATGCTTATG  AACTGAAACA  TGCCTTGAAG     300

GGAGCTGGAA  CAAATGAAAA  AGTACTGACA  GAAATTATTG  CTTCAAGGAC  ACCTGAAGAA     360

CTGAGAGCCA  TCAAACAAGT  TTATGAAGAA  GAATATGGCT  CAAGCCTGGA  AGATGACGTG     420

GTGGGGGACA  CTTCAGGGTA  CTACCAGCGG  ATGTTGGTGG  TTCTCCTTCA  GGCTAACAGA     480

GACCCTGATG  CTGGAATTGA  TGAAGCTCAA  GTTGAACAAG  ATGCTCAGGC  TTTATTTCAG     540

GCTGGAGAAC  TTAAATGGGG  GACAGATGAA  GAAAAGTTTA  TCACCATCTT  TGGAACACGA     600

AGTGTGTCTC  ATTTGAGAAA  GGTGTTTGAC  AAGTACATGA  CTATATCAGG  ATTTCAAATT     660

GAGGAAACCA  TTGACCGCGA  GACTTCTGGC  AATTTAGAGC  AACTACTCCT  TGCTGTTGTG     720

AAATCTATTC  GAAGTATACC  TGCCTACCTT  GCAGAGACCC  TCTATTATGC  TATGAAGGGA     780

GCTGGGACAG  ATGATCATAC  CCTCATCAGA  GTCATGGTTT  CCAGGAGTGA  GATTGATCTG     840

TTTAACATCA  GGAAGGAGTT  TAGGAAGAAT  TTTGCCACCT  CTCTTTATTC  CATGATTAAG     900

GGAGATACAT  CTGGGGACTA  TAAGAAAGCT  CTTCTGCTGC  TCTGTGGAGA  AGATGAC       957
```

(2) INFORMATION FOR SEQ ID NO:5:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (v) FRAGMENT TYPE: N-terminal (xi) SEQUENCE DESCRIPTION: SEQ ID NO:5:

```
Ala  Gln  Val  Leu  Arg  Gly  Thr  Val  Thr  Asp
1                 5                          10
```

We claim:

1. An isolated human DNA having a base sequence that encodes the following amino acid sequence:

Ala—Gln—Val—Leu—Arg—Gly—Thr—Val—Thr—Asp—Phe—Pro
Gly—Phe—Asp—Glu—Arg—Ala—Asp—Ala—Glu—Thr—Leu—Arg
Lys—Ala—Met—Lys—Gly—Leu—Gly—Thr—Asp—Glu—Glu—Ser
Ile—Leu—Thr—Leu—Leu—Thr—Ser—Arg—Ser—Asn—Ala—Gln
Arg—Gln—Glu—Ile—Ser—Ala—Ala—Phe—Lys—Thr—Leu—Phe
Gly—Arg—Asp—Leu—Leu—Asp—Asp—Leu—Lys—Ser—Glu—Leu
Thr—Gly—Lys—Phe—Glu—Lys—Leu—Ile—Val—Ala—Leu—Met
Lys—Pro—Ser—Arg—Leu—Tyr—Asp—Ala—Tyr—Glu—Leu—Lys
His—Ala—Leu—Lys—Gly—Ala—Gly—Thr—Asn—Glu—Lys—Val
Leu—Thr—Glu—Ile—Ile—Ala—Ser—Arg—Thr—Pro—Glu—Glu
Leu—Arg—Ala—Ile—Lys—Gln—Val—Tyr—Glu—Glu—Glu—Tyr
Gly—Ser—Ser—Leu—Glu—Asp—Asp—Val—Val—Gly—Asp—Thr
Ser—Gly—Tyr—Tyr—Gln—Arg—Met—Leu—Val—Val—Leu—Leu
Gln—Ala—Asn—Arg—Asp—Pro—Asp—Ala—Gly—Ile—Asp—Glu
Ala—Gln—Val—Glu—Gln—Asp—Ala—Gln—Ala—Leu—Phe—Gln
Ala—Gly—Glu—Leu—Lys—Trp—Gly—Thr—Asp—Glu—Glu—Lys
Phe—Ile—Thr—Ile—Phe—Gly—Thr—Arg—Ser—Val—Ser—His
Leu—Arg—Lys—Val—Phe—Asp—Lys—Tyr—Met—Thr—Ile—Ser
Gly—Phe—Gln—Ile—Glu—Glu—Thr—Ile—Asp—Arg—Glu—Thr
Ser—Gly—Asn—Leu—Glu—Gln—Leu—Leu—Leu—Ala—Val—Val
Lys—Ser—Ile—Arg—Ser—Ile—Pro—Ala—Tyr—Leu—Ala—Glu
Thr—Leu—Tyr—Tyr—Ala—Met—Lys—Gly—Ala—Gly—Thr—Asp
Asp—His—Thr—Leu—Ile—Arg—Val—Met—Val—Ser—Arg—Ser
Glu—Ile—Asp—Leu—Phe—Asn—Ile—Arg—Lys—Glu—Phe—Arg
Lys—Asn—Phe—Ala—Thr—Ser—Leu—Tyr—Ser—Met—Ile—Lys
Gly—Asp—Thr—Ser—Gly—Asp—Tyr—Lys—Lys—Ala—Leu—Leu
Leu—Leu—Cys—Gly—Glu—Asp—Asp.

2. The DNA of claim 1, wherein said nucleotide sequence is:

GCACAGGTTC TCAGAGGCAC TGTGACTGAC TTCCCTGGAT
TTGATGAGCG GGCTGATGCA GAAACTCTTC GGAAGGCTAT
GAAAGGCTTG GGCACAGATG AGGAGAGCAT CCTGACTCTG
TTGACATCCC GAAGTAATGC TCAGCGCCAG GAAATCTCTG
CAGCTTTTAA GACTCTGTTT GGCAGGGATC TTCTGGATGA
CCTGAAATCA GAACTAACTG GAAAATTTGA AAAATTAATT
GTGGCTCTGA TGAAACCCTC TCGGCTTTAT GATGCTTATG
AACTGAAACA TGCCTTGAAG GGAGCTGGAA CAAATGAAAA
AGTACTGACA GAAATTATTG CTTCAAGGAC ACCTGAAGAA
CTGAGAGCCA TCAAACAAGT TTATGAAGAA GAATATGGCT
CAAGCCTGGA AGATGACGTG GTGGGGGACA CTTCAGGGTA
CTACCAGCGG ATGTTGGTGG TTCTCCTTCA GGCTAACAGA
GACCCTGATG CTGGAATTGA TGAAGCTCAA GTTGAACAAG
ATGCTCAGGC TTTATTTCAG GCTGGAGAAC TTAAATGGGG
GACAGATGAA GAAAAGTTTA TCACCATCTT TGGAACACGA
AGTGTGTCTC ATTTGAGAAA GGTGTTTGAC AAGTACATGA
CTATATCAGG ATTTCAAATT GAGGAAACCA TTGACCGCGA
GACTTCTGGC AATTTAGAGC AACTACTCCT TGCTGTTGTG
AAATCTATTC GAAGTATACC TGCCTACCTT GCAGAGACCC
TCTATTATGC TATGAAGGGA GCTGGGACAG ATGATCATAC
CCTCATCAGA GTCATGGTTT CCAGGAGTGA GATTGATCTG
TTTAACATCA GGAAGGAGTT TAGGAAGAAT TTTGCCACCT
CTCTTTATTC CATGATTAAG GGAGATACAT CTGGGGACTA
TAAGAAAGCT CTTCTGCTGC TCTGTGGAGA AGATGAC.

3. A recombinant plasmid comprising:

a human DNA having a nucleotide sequence that encodes the following amino acid sequence:

Ala—Gln—Val—Leu—Arg—Gly—Thr—Val—Thr—Asp—Phe—Pro
Gly—Phe—Asp—Glu—Arg—Ala—Asp—Ala—Glu—Thr—Leu—Arg
Lys—Ala—Met—Lys—Gly—Leu—Gly—Thr—Asp—Glu—Glu—Ser
Ile—Leu—Thr—Leu—Leu—Thr—Ser—Arg—Ser—Asn—Ala—Gln
Arg—Gln—Glu—Ile—Ser—Ala—Ala—Phe—Lys—Thr—Leu—Phe

-continued
Gly—Arg—Asp—Leu—Leu—Asp—Asp—Leu—Lys—Ser—Glu—Leu
Thr—Gly—Lys—Phe—Glu—Lys—Leu—Ile—Val—Ala—Leu—Met
Lys—Pro—Ser—Arg—Leu—Tyr—Asp—Ala—Tyr—Glu—Leu—Lys
His—Ala—Leu—Lys—Gly—Ala—Gly—Thr—Asn—Glu—Lys—Val
Leu—Thr—Glu—Ile—Ile—Ala—Ser—Arg—Thr—Pro—Glu—Glu
Leu—Arg—Ala—Ile—Lys—Gln—Val—Tyr—Glu—Glu—Glu—Tyr
Gly—Ser—Ser—Leu—Glu—Asp—Asp—Val—Val—Gly—Asp—Thr
Ser—Gly—Tyr—Tyr—Gln—Arg—Met—Leu—Val—Val—Leu—Leu
Gln—Ala—Asn—Arg—Asp—Pro—Asp—Ala—Gly—Ile—Asp—Glu
Ala—Gln—Val—Glu—Gln—Asp—Ala—Gln—Ala—Leu—Phe—Gln
Ala—Gly—Glu—Leu—Lys—Trp—Gly—Thr—Asp—Glu—Glu—Lys
Phe—Ile—Thr—Ile—Phe—Gly—Thr—Arg—Ser—Val—Ser—His
Leu—Arg—Lys—Val—Phe—Asp—Lys—Tyr—Met—Thr—Ile—Ser
Gly—Phe—Gln—Ile—Glu—Glu—Thr—Ile—Asp—Arg—Glu—Thr
Ser—Gly—Asn—Leu—Glu—Gln—Leu—Leu—Leu—Ala—Val—Val
Lys—Ser—Ile—Arg—Ser—Ile—Pro—Ala—Tyr—Leu—Ala—Glu
Thr—Leu—Tyr—Tyr—Ala—Met—Lys—Gly—Ala—Gly—Thr—Asp
Asp—His—Thr—Leu—Ile—Arg—Val—Met—Val—Ser—Arg—Ser
Glu—Ile—Asp—Leu—Phe—Asn—Ile—Arg—Lys—Glu—Phe—Arg
Lys—Asn—Phe—Ala—Thr—Ser—Leu—Tyr—Ser—Met—Ile—Lys
Gly—Asp—Thr—Ser—Gly—Asp—Tyr—Lys—Lys—Ala—Leu—Leu
Leu—Leu—Cys—Gly—Glu—Asp—Asp;

and a replicative vector DNA.

4. The recombinant plasmid as claimed in claim 3, wherein said recombinant plasmid comprises the following regions (1)–(6) in order in the downstream direction of transcription:

(1) a promoter;

(2) a ribosome-binding site;

(3) an initiation codon;

(4) a DNA having a nucleotide sequence that encodes the following amino acid sequence (SEQ ID NO:1):

Ala—Gln—Val—Leu—Arg—Gly—Thr—Val—Thr—Asp—Phe—Pro
Gly—Phe—Asp—Glu—Arg—Ala—Asp—Ala—Glu—Thr—Leu—Arg
Lys—Ala—Met—Lys—Gly—Leu—Gly—Thr—Asp—Glu—Glu—Ser
Ile—Leu—Thr—Leu—Leu—Thr—Ser—Arg—Ser—Asn—Ala—Gln
Arg—Gln—Glu—Ile—Ser—Ala—Ala—Phe—Lys—Thr—Leu—Phe
Gly—Arg—Asp—Leu—Leu—Asp—Asp—Leu—Lys—Ser—Glu—Leu
Thr—Gly—Lys—Phe—Glu—Lys—Leu—Ile—Val—Ala—Leu—Met
Lys—Pro—Ser—Arg—Leu—Tyr—Asp—Ala—Tyr—Glu—Leu—Lys
His—Ala—Leu—Lys—Gly—Ala—Gly—Thr—Asn—Glu—Lys—Val
Leu—Thr—Glu—Ile—Ile—Ala—Ser—Arg—Thr—Pro—Glu—Glu
Leu—Arg—Ala—Ile—Lys—Gln—Val—Tyr—Glu—Glu—Glu—Tyr
Gly—Ser—Ser—Leu—Glu—Asp—Asp—Val—Val—Gly—Asp—Thr
Ser—Gly—Tyr—Tyr—Gln—Arg—Met—Leu—Val—Val—Leu—Leu
Gln—Ala—Asn—Arg—Asp—Pro—Asp—Ala—Gly—Ile—Asp—Glu
Ala—Gln—Val—Glu—Gln—Asp—Ala—Gln—Ala—Leu—Phe—Gln
Ala—Gly—Glu—Leu—Lys—Trp—Gly—Thr—Asp—Glu—Glu—Lys
Phe—Ile—Thr—Ile—Phe—Gly—Thr—Arg—Ser—Val—Ser—His
Leu—Arg—Lys—Val—Phe—Asp—Lys—Tyr—Met—Thr—Ile—Ser
Gly—Phe—Gln—Ile—Glu—Glu—Thr—Ile—Asp—Arg—Glu—Thr
Ser—Gly—Asn—Leu—Glu—Gln—Leu—Leu—Leu—Ala—Val—Val
Lys—Ser—Ile—Arg—Ser—Ile—Pro—Ala—Tyr—Leu—Ala—Glu
Thr—Leu—Tyr—Tyr—Ala—Met—Lys—Gly—Ala—Gly—Thr—Asp
Asp—His—Thr—Leu—Ile—Arg—Val—Met—Val—Ser—Arg—Ser
Glu—Ile—Asp—Leu—Phe—Asn—Ile—Arg—Lys—Glu—Phe—Arg
Lys—Asn—Phe—Ala—Thr—Ser—Leu—Tyr—Ser—Met—Ile—Lys
Gly—Asp—Thr—Ser—Gly—Asp—Tyr—Lys—Lys—Ala—Leu—Leu
Leu—Leu—Cys—Gly—Glu—Asp—Asp;

(5) a termination codon; and (6) a transcription terminator.

5. A transformant containing a recombinant plasmid which comprises a human DNA fragment having a base sequence that encodes the following amino acid sequence (SEQ ID NO:1):

Ala—Gln—Val—Leu—Arg—Gly—Thr—Val—Thr—Asp—Phe—Pro
Gly—Phe—Asp—Glu—Arg—Ala—Asp—Ala—Glu—Thr—Leu—Arg
Lys—Ala—Met—Lys—Gly—Leu—Gly—Thr—Asp—Glu—Glu—Ser
Ile—Leu—Thr—Leu—Leu—Thr—Ser—Arg—Ser—Asn—Ala—Gln
Arg—Gln—Glu—Ile—Ser—Ala—Ala—Phe—Lys—Thr—Leu—Phe
Gly—Arg—Asp—Leu—Leu—Asp—Asp—Leu—Lys—Ser—Glu—Leu
Thr—Gly—Lys—Phe—Glu—Lys—Leu—Ile—Val—Ala—Leu—Met
Lys—Pro—Ser—Arg—Leu—Tyr—Asp—Ala—Tyr—Glu—Leu—Lys
His—Ala—Leu—Lys—Gly—Ala—Gly—Thr—Asn—Glu—Lys—Val
Leu—Thr—Glu—Ile—Ile—Ala—Ser—Arg—Thr—Pro—Glu—Glu
Leu—Arg—Ala—Ile—Lys—Gln—Val—Tyr—Glu—Glu—Glu—Tyr
Gly—Ser—Ser—Leu—Glu—Asp—Asp—Val—Val—Gly—Asp—Thr
Ser—Gly—Tyr—Tyr—Gln—Arg—Met—Leu—Val—Val—Leu—Leu
Gln—Ala—Asn—Arg—Asp—Pro—Asp—Ala—Gly—Ile—Asp—Glu
Ala—Gln—Val—Glu—Gln—Asp—Ala—Gln—Ala—Leu—Phe—Gln
Ala—Gly—Glu—Leu—Lys—Trp—Gly—Thr—Asp—Glu—Glu—Lys
Phe—Ile—Thr—Ile—Phe—Gly—Thr—Arg—Ser—Val—Ser—His
Leu—Arg—Lys—Val—Phe—Asp—Lys—Tyr—Met—Thr—Ile—Ser
Gly—Phe—Gln—Ile—Glu—Glu—Thr—Ile—Asp—Arg—Glu—Thr
Ser—Gly—Asn—Leu—Glu—Gln—Leu—Leu—Leu—Ala—Val—Val
Lys—Ser—Ile—Arg—Ser—Ile—Pro—Ala—Tyr—Leu—Ala—Glu
Thr—Leu—Tyr—Tyr—Ala—Met—Lys—Gly—Ala—Gly—Thr—Asp
Asp—His—Thr—Leu—Ile—Arg—Val—Met—Val—Ser—Arg—Ser
Glu—Ile—Asp—Leu—Phe—Asn—Ile—Arg—Lys—Glu—Phe—Arg
Lys—Asn—Phe—Ala—Thr—Ser—Leu—Tyr—Ser—Met—Ile—Lys
Gly—Asp—Thr—Ser—Gly—Asp—Tyr—Lys—Lys—Ala—Leu—Leu;

and a replicative vector DNA.

6. The transformant of claim 5, wherein said plasmid comprises the following regions (1)–(6), in order, in the downstream direction of transcription:

(1) a promoter;

(2) a ribosome-binding site;

(3) an initiation codon;

(4) a DNA having a nucleotide sequence that encodes the following amino acid sequence (SEQ ID NO:1):

Ala—Gln—Val—Leu—Arg—Gly—Thr—Val—Thr—Asp—Phe—Pro
Gly—Phe—Asp—Glu—Arg—Ala—Asp—Ala—Glu—Thr—Leu—Arg
Lys—Ala—Met—Lys—Gly—Leu—Gly—Thr—Asp—Glu—Glu—Ser
Ile—Leu—Thr—Leu—Leu—Thr—Ser—Arg—Ser—Asn—Ala—Gln
Arg—Gln—Glu—Ile—Ser—Ala—Ala—Phe—Lys—Thr—Leu—Phe
Gly—Arg—Asp—Leu—Leu—Asp—Asp—Leu—Lys—Ser—Glu—Leu
Thr—Gly—Lys—Phe—Glu—Lys—Leu—Ile—Val—Ala—Leu—Met
Lys—Pro—Ser—Arg—Leu—Tyr—Asp—Ala—Tyr—Glu—Leu—Lys
His—Ala—Leu—Lys—Gly—Ala—Gly—Thr—Asn—Glu—Lys—Val
Leu—Thr—Glu—Ile—Ile—Ala—Ser—Arg—Thr—Pro—Glu—Glu
Leu—Arg—Ala—Ile—Lys—Gln—Val—Tyr—Glu—Glu—Glu—Tyr
Gly—Ser—Ser—Leu—Glu—Asp—Asp—Val—Val—Gly—Asp—Thr
Ser—Gly—Tyr—Tyr—Gln—Arg—Met—Leu—Val—Val—Leu—Leu
Gln—Ala—Asn—Arg—Asp—Pro—Asp—Ala—Gly—Ile—Asp—Glu
Ala—Gln—Val—Glu—Gln—Asp—Ala—Gln—Ala—Leu—Phe—Gln
Ala—Gly—Glu—Leu—Lys—Trp—Gly—Thr—Asp—Glu—Glu—Lys
Phe—Ile—Thr—Ile—Phe—Gly—Thr—Arg—Ser—Val—Ser—His
Leu—Arg—Lys—Val—Phe—Asp—Lys—Tyr—Met—Thr—Ile—Ser
Gly—Phe—Gln—Ile—Glu—Glu—Thr—Ile—Asp—Arg—Glu—Thr
Ser—Gly—Asn—Leu—Glu—Gln—Leu—Leu—Leu—Ala—Val—Val
Lys—Ser—Ile—Arg—Ser—Ile—Pro—Ala—Tyr—Leu—Ala—Glu
Thr—Leu—Tyr—Tyr—Ala—Met—Lys—Gly—Ala—Gly—Thr—Asp
Asp—His—Thr—Leu—Ile—Arg—Val—Met—Val—Ser—Arg—Ser
Glu—Ile—Asp—Leu—Phe—Asn—Ile—Arg—Lys—Glu—Phe—Arg
Lys—Asn—Phe—Ala—Thr—Ser—Leu—Tyr—Ser—Met—Ile—Lys
Gly—Asp—Thr—Ser—Gly—Asp—Tyr—Lys—Lys—Ala—Leu—Leu
Leu—Leu—Cys—Gly—Glu—Asp—Asp;

(5) a termination codon; and (6) a transcription terminator.

* * * * *